United States Patent
Serebruany et al.

(10) Patent No.: US 6,245,782 B1
(45) Date of Patent: *Jun. 12, 2001

(54) METHODS OF INHIBITING PLATELET ACTIVATION WITH SELECTIVE SEROTONIN REUPTAKE INHIBITORS

(75) Inventors: Victor L. Serebruany, Ellicott City; Paul A. Gurbel, Baltimore, both of MD (US); Christopher M. O'Connor, Durham, NC (US)

(73) Assignee: Heartdrug Research L.L.C., Ellicott City, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/312,987

(22) Filed: May 17, 1999

(51) Int. Cl.$^7$ .................. A61K 31/445; A61K 31/34; A61K 31/15; A61K 31/135; A61K 31/03

(52) U.S. Cl. .................. 514/321; 514/469; 514/640; 514/654; 514/753

(58) Field of Search .................. 514/753, 640, 514/321, 469, 654

(56) References Cited

U.S. PATENT DOCUMENTS

| | | |
|---|---|---|
| 4,536,518 | 8/1985 | Welch, Jr. et al. ............ 514/647 |
| 4,650,884 | 3/1987 | Bogeso ...................... 549/467 |
| 4,721,723 | 1/1988 | Barnes et al. ............... 514/321 |
| 4,940,731 | 7/1990 | Bick ......................... 514/657 |
| 4,943,590 | 7/1990 | Boegesoe et al. ............. 514/469 |
| 4,962,128 | 10/1990 | Doogan et al. .............. 514/647 |
| 5,130,338 | 7/1992 | Bacopoulos et al. .......... 514/646 |
| 5,248,699 | 9/1993 | Sysko et al. ................ 514/647 |
| 5,296,507 * | 3/1994 | Tanaka et al. ............... 514/465 |
| 5,371,092 | 12/1994 | Johnson ..................... 514/321 |
| 5,436,272 | 7/1995 | Scheinbaum et al. .......... 514/646 |
| 5,587,398 | 12/1996 | Elmaleh et al. .............. 514/654 |
| 5,589,511 | 12/1996 | Young et al. ................ 514/646 |
| 5,648,396 | 7/1997 | Young et al. ................ 514/651 |
| 5,708,035 | 1/1998 | Young et al. ................ 514/649 |
| 5,760,243 | 6/1998 | Theriot ...................... 548/240 |
| 5,830,500 | 11/1998 | El-Rashidy et al. ........... 424/465 |
| 5,856,493 | 1/1999 | Ward et al. .................. 546/197 |
| 5,872,132 | 2/1999 | Ward et al. .................. 514/321 |

FOREIGN PATENT DOCUMENTS

| | | |
|---|---|---|
| 768083A2 | 4/1997 | (EP) . |
| WO 98/19512 | 5/1998 | (WO) . |
| WO 98/19513 | 5/1998 | (WO) . |

OTHER PUBLICATIONS

Atar, D., et al., "Effects of magnesium supplementation in a porcine model of myocardial ischemia and reperfusion," *J. Cardiovasc. Pharmacol.*, 24(4): 603–611 (1994).

Block, K.L, and Poncz, M., "Platelet glycoprotein IIb gene expression as a model of megakaryocyte–specific expression," *Stem Cells*, 13(2): 135–145 (1995).

Dwyer, S.D., and Meyers, K.M., "Anesthetics and anticoagulants used in the preparation of rat platelet–rich–plasma alter rat platelet aggregation," Thromb. Res., 42(2): 139–151 (1986).

Heindl, B., et al., "The volatile anesthetic sevoflurane mitigates cardiodepressive effects of platelets in reperfused hearts," *Basic Res. Cardiol.*, 94(2): 102–111 (1999).

Kinlough–Rathbone, R.L., et al., "Rabbit and rat platelets do not respond to thrombin receptor peptides that activate human platelets," *Blood*, 82(1): 103–106 (1993).

Knight, D.M., et al., "The immunogenicity of the 7E3 murine monoclonal Fab antibody fragment variable region is dramatically reduced in humans by substitution of human for murine constant regions," *Mol. Immunol.*, 32(16): 1271–1281 (1995).

Koerner, J.E., et al., "Protection against postischemic myocardial dysfunction in anesthetized rabbits with scavengers of oxygen–derived free radicals: superoxide dismutase plus catalase, N–2–mercaptopropionyl glycine and captopril," *J. Cardiovasc. Pharmacol.*, 17(2): 185–191 (1991).

Lipscomb, D.L., et al., "DNA sequence of the canine platelet $\beta 3$ gene from cDNA: comparison of canine and mouse $\beta 3$ to segments that encode alloantigenic sites and functional domains of $\beta 3$ in human beings," *J. Lab. Clin. Med.*, 134(3): 313–321 (1999).

Serebruany, V.L., et al., "Crossreactivity of Human versus Swine Platelet Surface Antigens is Similar for Glycoproteins Ib and IIIa, but Not for the Glycoprotein IIb/IIIa Complex," *J. Thromb. Thrombolysis*, 5(1): 37–41 (1998).

Sprouse, J., et al., "Comparison of the effects of sertraline and its metabolite desmethylsertraline on blockade of central 5–HT reuptake in vivo," *Neuropsychopharmacology*, 14(4): 225–231 (1996).

Tan, P.Z., et al., "Characterization of radioactive metabolites of 5–HT$_{2A}$ receptor PET ligand[$^{18}$F]altanserin in human and rodent," *Nucl. Med. Biol.*, 26(6): 601–608 (1999).

Vollenweider, F.X., et al., "Opposite effects of 3, 4–methylenedioxymethamphetamine (MDMA) on sensorimotor gating in rats versus healthy humans," *Psychopharmacology*, 143(4): 365–372 (1999).

Namm, D.H., et al., "Species Specificity of the Platelet responses to 1–0–alkyl–2–acetyl–sn–glycero–3– phosphocholine," *Thromb. Res.*, 25(4) 341–350 (1982).

(List continued on next page.)

Primary Examiner—Rebecca Cook
(74) *Attorney, Agent, or Firm*—Hamilton, Brook, Smith & Reynolds, P.C.

(57) ABSTRACT

The present invention pertains to methods for reducing the platelet activation state in an individual comprising administering a selective serotonin reuptake inhibitor (SSRI). The platelet activation state is reduced upon administering a SSRI, as measured by one or more platelet activation markers. The invention also relates to methods for treating or preventing an individual at risk for a vascular event, disease or disorder by administering a SSRI.

24 Claims, 7 Drawing Sheets

OTHER PUBLICATIONS

De Clerck, F., "Effects of Serotonin on Platelets and Blood Vessels," *Journal of Cardiovascular Pharmacology*, 17(Suppl.5):S1–S5 (1991).

Vanhoutte, P.M., "Platelet–Derived Serotonin, the Endothelium, and Cardiovascular Disease," *Journal of Cardiovascular Pharmacology*, 17(Suppl. 5):S6–S12 (1991).

McAdams, C., et al., "Alteration by a Plasma Factor of Platelet Aggregation and 5HT Uptake in Depression," *Biol Psychiatry*, 32:296–298 (1992).

Doogan, D.P., and Caillard, V., "Sertraline in the Prevention of Depression," *Brit. J. Psychiat.*, 160:217–222 (1992).

Bakish, D., et al., "Effects of Selective Serotonin Reuptake Inhibitors on Platelet Serotonin Parameters in Major Depressive Disorder," *Biol. Psychiatry*, 41:184–190 (1997).

Helmeste, D.M., et al., "Serotonin uptake inhibitors modulate intracellular $Ca^{2+}$ mobilization in platelets," *European Journal of Pharmacology*, 288:373–377 (1995).

Glassman, A.H., and Shapiro, P.A., "Depression and the Course of Coronary Artery Disease," *Am. J. Psychiatry*, 155:4–11 (1998).

Golino, P., et al., "Local Effect of Serotonin Released During Coronary Angioplasty," *N. Engl. J. Med.*, 330(8):523–528 (1994).

Ronfeld, R.A., et al., "Sertraline–Chronopharmacokinetics and the Effect of Coadministration with Food," *Clin. Pharmacokinet.*, 32:50–55 (1997).

Schleifer, S.J., et al., "The Nature and Course of Depression Following Myocardial Infarction," *Arch Intern Med*, 149:1785–1789 (1989).

Kundu, S.K., et al., "Description of an In Vitro Platelet Function Analyzer–PFA–100™," *Seminars in Thrombosis and Hemostasis*, 21(Suppl.2):106–113 (1995).

Fressinaud, E., et al., "Screening for von Willebrand Disease With a New Analyzer Using High Shear Stress: A Study of 60 Cases," *Blood*, 91(4):1325–1331 (Feb. 15, 1998).

Bourdeaux, R., et al., "Effects of Fluoxetine and Norfluoxetine on 5–Hydroxytryptamine Metabolism in Blood Platelets and Brain after Administration to Rats," *J. Pharm. Pharmacol.*, 50:1387–1392 (1998).

Pai, V.B., and Kelly, M.W., "Bruising Associate with the Use of Fluoxetine," *Ann. Pharmacother.*, 30:786–788 (1996).

Frasure–Smith, N., et al., "Depression Following Myocardial Infarction–Impact on 6–Month Survival," *JAMA*, 270:1819–1825 (1993).

Frasure–Smith, N., et al., "Depression and 18–Month Prognosis After Myocardial Infarction," *Circulation*, 91:999–1005 (1995).

Hopcroft, K., "Going home after a heart attack–Depression is also a risk factor," *Brit. Med. J.*, 313:754 (1996).

Markowitz, J.H., et al., "Platelets and Coronary Heart Disease: Potential Psychophysiologic Mechanisms," *Psychosom. Med.*, 53:643–668 (1991).

Mehta, J., and Mehta, P., "Role of Blood Platelets and Prostaglandins in Coronary Artery Disease," *Am. J. Cardiol.*, 48:366–373 (1981).

Carney, R.M., et al., "Major Depressive Disorders in Coronary Artery Disease," *Am. J. Cardiol.*, 60:1273–1275 (1987).

Ahern, D.K., et al., "Biobehavioral Variables and Mortality or Cardiac Arrest in the Cardiac Arrhythmia Pilot Study (CAPS)," *Am. J. Cardiol.*, 66:59–62 (1990).

Meltzer, H.Y., and Lowy, M.T., "The Serotonin Hypothesis of Depression. In: *Psychopharmacology: The Third Generation of Progress*," Raven Press, 513–526 (1987).

Musselman, D.L., et al., "Exaggerated Platelet Reactivity in Major Depression," *Am. J. Psychiatry*, 153:1313–1317 (1996).

Briley, M.S., et al., "[$^3$H]–Imipramine Binding in Human Platelets: a New Biochemical Parameter in Depression," *Neuropharmacology*, 19:1209–1210 (1980).

Hrdina, P.D., et al., "Platelet serotonergic indicies in major depression: up–regulation of $5-HT_{2A}$ receptors unchanged by antidepressant treatment," *Psychiatr. Res.*, 66:73–85 (1997).

Doogan, D.P., and Caillard, V., "Sertraline: A New Antidepressant," *J. Clin. Psychiatry*, 49(8 Suppl):46–51 (1988).

Tuomisto, J., et al., "Decreased Uptake of 5–Hydroxytryptamine in Blood Platelets from Patients with Endogenous Depression," *Psychopharmacology*, 65:141–147 (1979).

Coppen, A., et al., "Platelet 5–Hydroxytryptamine Accumulation in Depressive Illness," *Clin. Chim. Acta*, 87:165–168 (1978).

Biegon, A., et al., "Serotonin 5–HT2 receptor binding on blood platelets—a peripheral marker for depression", *Life Sci.*, 41(22):2485–2492 (1987).

Sheline, Y.I., et al., "Platelet Serotonin Markers and Depressive Symptomatology," *Biol. Psychiatry*, 37:442–447 (1995).

Konopka, L.M., et al., "Serotonin–Induced Increases in Platelet Cytosolic Calcium Concentration in Depressed, Schizophrenic, and Substance Abuse Patients," *Biol. Psychiatry*, 39:708–713 (1996).

Nugent, D.F., et al., "Alteration by a plasma factor(s) of platelet aggregation in unmedicated unipolar depressed patients," *J. Affect Disord.*, 31:61–66 (1994).

Nugent, D.F., et al., "Further characterization of the inhibition of platelet aggregation by a plasma factor(s) in unmedicated unipolar depressed patients," *J. Affect Disord.*, 33:227–231 (1995).

Maes, M., et al., "Blood coagulation and platelet aggregation in major depression," *J. Affect Disord.*, 40:35–40 (1996).

Karege, F., et al., "Adrenaline–Induced Platelet Aggregation in Depressed Patients and Control Subjects," *Neuropsychobiology*, 27:21–25 (1993).

Musselman, D.L., et al., "The Relationship of Depression to Cardiovascular Disease: Epidemiology, Biology, and Treatment," *Arch. Gen. Psychiatry*, 55:580–592 (1998).

Cleophas, T.J.M., "Depression and Myocardial Infarction," *Drugs & Aging*, 11:111–118 (1997).

Koe, B.K., "Preclinical Pharmacology of Sertraline: A Potent and Specific Inhibitor of Serotonin Reuptake," *J. Clin. Psyciatry*, 51[12, suppl B]:13–17 (1990).

Rickels, K., and Schweizer, E., "Clinical Overview of Serotonin Reuptake Inhibitors," *J. Clin. Psychiatry*, 51:12(suppl B):9–12 (1990).

Baumann, P., "Pharmacokynetic–Pharmacodynamic Relationship of the Selective Serotonin Reuptake Inhibitors," *Clin. Pharmacokinet*, 6:444–469 (1996).

Shelton, R.C., "The Role of Sertraline in the Management of Depression," *Clin. Ther.*, 16:768–782 (1994).

Nair, G.V. et al., "Depression, Coronary Events, Platelet Inhibition, and Serotonin Reuptake Inhibitors", *The Am. J. or Cardiology*, 84:321–323 (1999).

Reimherr, F.W., et al., "A double–blind, placebo– and amitriptyline–controlled, multicenter comparison study in outpatients with major depression", *J. Clin. Psychiat.,* 51:12(Suppl B):18–27 (1990).

Roose, S.P., and Glassman, A.H., "Antidepressant Choice in the Patient With Cardiac Disease: Lessons From the Cardiac Arrhythmia Suppression Trial (CAST) Studies," *J Clin Psychiatry,* 55(9,suppl A):83–87 (1994).

Bakish, D., et al., "Effects of Selective Serotonin Reuptake Inhibitors on Platelet Serotonin Parameters in Major Depressive Disorder," *Biol. Psychiatry,* 41:184–190 (1997).

Butler, J., et al., "The Platelet Serotonergic System in Depression and Following Sertraline Treatment", *Int. Clin. Psychopharmacol,* 3:343–347 (1988).

Phillips, O.M., et al., "Kinetics of the Interaction of Sertraline with the Human Platelet Plasma Membrane 5–hydroxytryptamine Carrier," *Eur. J. Pharmacol.,* 146:299–306 (1988).

Zoloft ®,Physicians Desk Reference, Arky, R.,Med. Consultant, 53:2443 (1999).

Serebruany, V.L., et al., "Depressed Platelet Status in an Elderly Patient With Hemorrhagic Stroke After Thrombolysis for Acute Myocardial Infarction," *Stroke,* 29:235–238 (1998).

Willerson, J.T., et al., "Role of Thromboxane and Serotonin as Mediators in the Development of Spontaneous Alternations in Coronary Blood Flow and Neointimal Proliferation in Canine Models with Chronic Coronary Artery Stenoses and Endothelial Injury," *J. Am. Coll. Cardiol.,* 17:101B–110B (1991).

Pakala, R., et al., "Effect of Serotonin, Thromboxane $A_2$, and Specific Receptor Antagonists on Vascular Smooth Muscle Cell Proliferation," *Circulation,* 96:2280–2286 (1997).

Serebruany, V.L., et al., "Heterogeneity of platelet aggregation and major surface receptor expression in patients with acute myocardial infarction," *Am. Heart J.,* 136:398–405 (1998).

* cited by examiner

METHODS OF INHIBITING PLATELET ACTIVATION WITH SELECTIVE SEROTONIN REUPTAKE INHIBITORS

BACKGROUND OF THE INVENTION

Coronary Heart Disease (CHD) is one of the most common diagnoses of hospital patients in the United States, with over five million cases occurring yearly. Platelet activation plays an important role in a variety of vascular events, diseases and disorders. When trauma of the blood vessel wall occurs, a series of reactions also occur. A clot, also referred to as a thrombus, is involved in many vascular diseases including cardiovascular (e.g., heart failure) and cerebrovascular diseases (e.g., stroke). Vascular diseases that result from the activation of platelets pose serious problems to patients and the physicians who treat them. Physicians continue to search for better preventative and/or curative treatments for vascular diseases that are associated with platelet activation.

Hence, a need exists for new and improved treatment options for individuals who have vascular diseases. Additionally, a need exists for therapies which target receptors that are involved in and/or cause platelet activation.

SUMMARY OF THE INVENTION

The present invention pertains to methods of reducing the platelet activation state of an individual. The methods comprise administering to the individual an effective amount of at least one serotonin inhibitor or antagonist. In one embodiment, the serotonin inhibitor or antagonist is a selective serotonin reuptake inhibitor (SSRI) (e.g., sertraline, fluvoxamine, paroxetine, citalopram, fluoxetine or metabolites thereof). The SSRI can be administered, for example, orally, intravenously, intramuscularly, subcutaneously, parenterally, nasally, by inhalation, by implant, by injection, or by suppository. In particular, sertraline, fluoxamine, paroxetine, citalopram or fluoxetine can be administered orally in an amount between about 10 mg–2500 mg/daily. Upon administration of a SSRI, the platelet activation state is reduced. The platelet activation state is assessed by measuring at least one platelet activation marker. One or more platelet activation markers is reduced by at least about 10% (e.g., by 20%, 30%, 40%, 50%, 60%, 70%, 80%, or 90%), and is indicative of a reduction in the platelet activation state. Examples of platelet activation markers are: CD9, GPIb, GPIIb, GPIIIa, CDIa–IIa, P-selectin, PECAM-1, GPIIb/IIIa, vitronectin receptor, other integrins and adhesive molecules.

Another embodiment of the present invention includes methods of preventing or treating an individual at risk for one or more vascular events, diseases or disorders. These methods comprise administering to an individual an effective amount of at least one serotonin inhibitor or antagonist, wherein the platelet activation state is reduced. A SSRI such as sertraline, fluvoxamine, paroxetine, citalopram, fluoxetine or metabolites thereof can be administered. Some examples of vascular events, diseases or disorders are myocardial infarction, angina, stroke, pulmonary embolism, transient ischemic attack, deep vein thrombosis, thrombotic re-occlusion subsequent to a coronary intervention procedure, heart surgery or vascular surgery, peripheral vascular thrombosis, Syndrome X, heart failure, and a disorder in which a narrowing of at least one coronary artery occurs. The platelet activation state is reduced, which is assessed with the measurement of platelet activation markers. At least one platelet activation marker (e.g., CD9, GPIb, GPIIb, GPIIIa, CDIa–IIa, P-selectin, PECAM-1, GPIIb/IIIa, vitronectin receptor, other integrins or adhesive molecules) decreases (e.g., by 10%, 20%, 30%, 40%, 50%, 60%, 70%, 80%, or 90%) as compared to the level of the platelet activation marker just prior to administration to an individual who has an active or elevated platelet activation state. When administering a SSRI to an individual to prevent a vascular event, disease or disorder, the platelet activation state can be prevented from increasing (e.g., remain at same level or decrease), as measured by platelet activation markers. In particular, the present invention pertains to methods of treating an individual with or preventing an individual from having coronary heart disease.

The present invention includes administration of a SSRI together with other drugs or compositions used to treat or prevent vascular events, diseases, or disorders; or other drugs used to reduce or inhibit platelet activation. Hence, another embodiment of the present invention relates to methods of preventing or treating an individual at risk for a vascular event, disease or disorder, that comprise administering to the individual an effective amount of a serotonin inhibitor or antagonist (e.g., a SSRI), and at least one other composition used for treating or preventing a vascular event, wherein the platelet activation state decreases. Examples of drugs or compositions that can be administered with a SSRI are aspirin, heparin, thienopyridines and GPIIb/IIIa inhibitors.

The methods further include inhibiting or reducing platelet activation by contacting platelets with a selective serotonin reuptake inhibitor in an amount sufficient to inhibit or reduce platelet activation. The platelet activation state is indicated by a reduction in one or more platelet activation markers (e.g., CD 9, GPIb, GPIIb, GPIIIa, CDIa–IIa, P-selectin, PECAM-1, GPIIb/IIIa, vitronectin receptor, other integrins and adhesive molecules).

The present invention takes advantage of the discovery that serotonin plays a role in platelet activation. The present invention provides effective treatment options for individuals that have vascular diseases by targeting serotonin activity.

or collagen in Platelet Rich Plasma (PRP) from a post-coronary angioplasty patient incubated with N-desmethylsertraline (NDMS) at 31.1, 64.1, 143.0 ng/ml.

Figure 7:
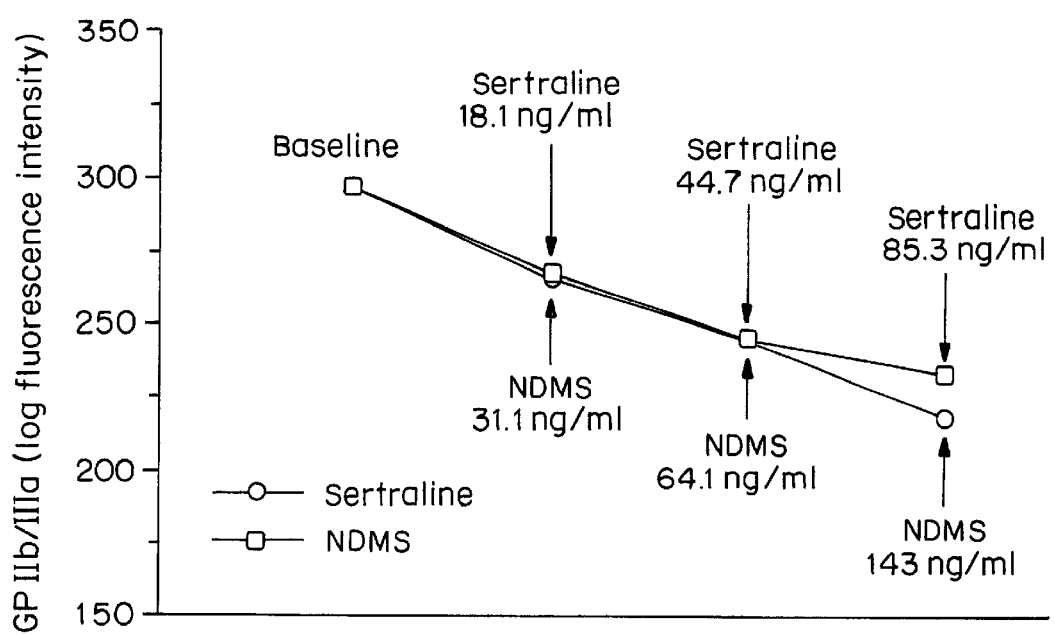

FIG. 7 is a graph showing the log fluorescence intensity of GPIIb/IIIa after incubation of whole blood with sertraline at 18.1, 44.7 or 85.3 ng/ml; or N-desmethylsertraline (NDMS) at 31.1, 64.1, 143.0 ng/ml from a post-coronary angioplasty patient.

Figure 8:
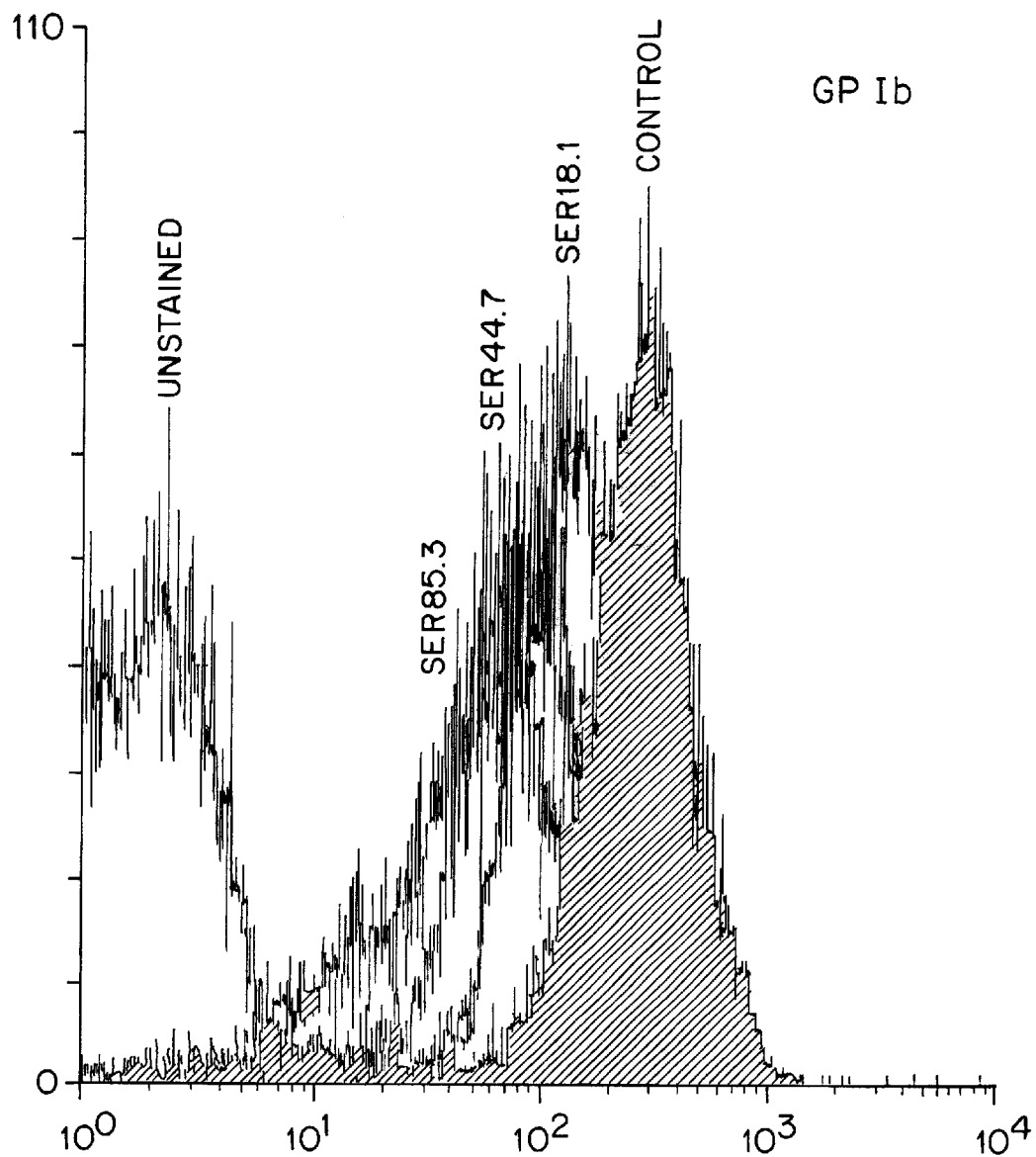

FIG. 8 is a graph from a flow cytometer showing the level of platelet GPIb expression when subjected to a control, 18.1 ng/mL, 44.7 ng/mL or 85.5 ng/mL of sertraline, or unstained cells.

Figure 9:
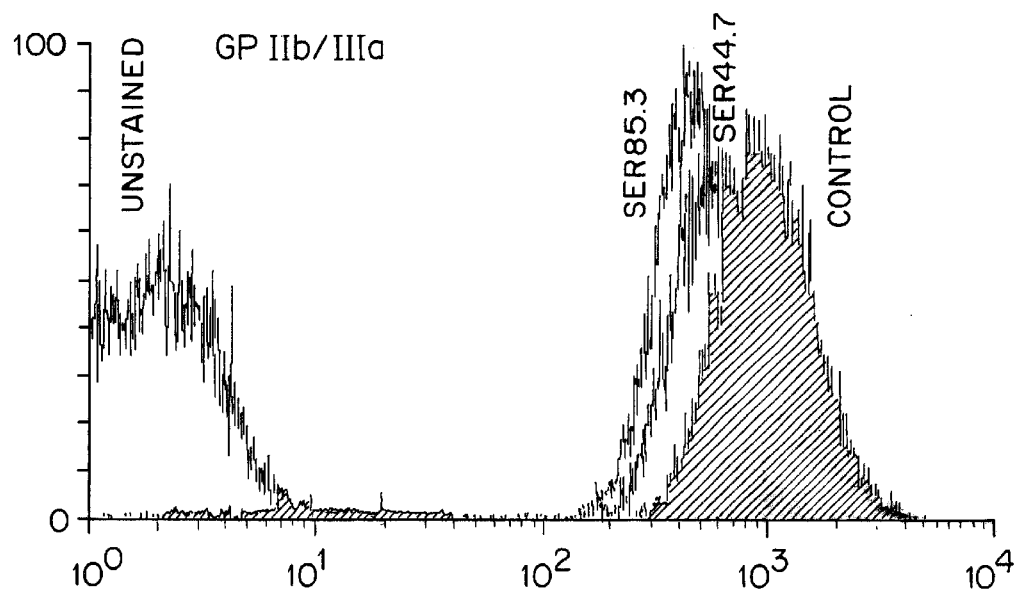

FIG. 9 is a graph from a flow cytometer showing the level of GPIIb/III a expression when subjected to a control, 44.7 ng/mL of sertraline, 85.3 ng/mL of sertraline or unstained cells.

Figure 10:
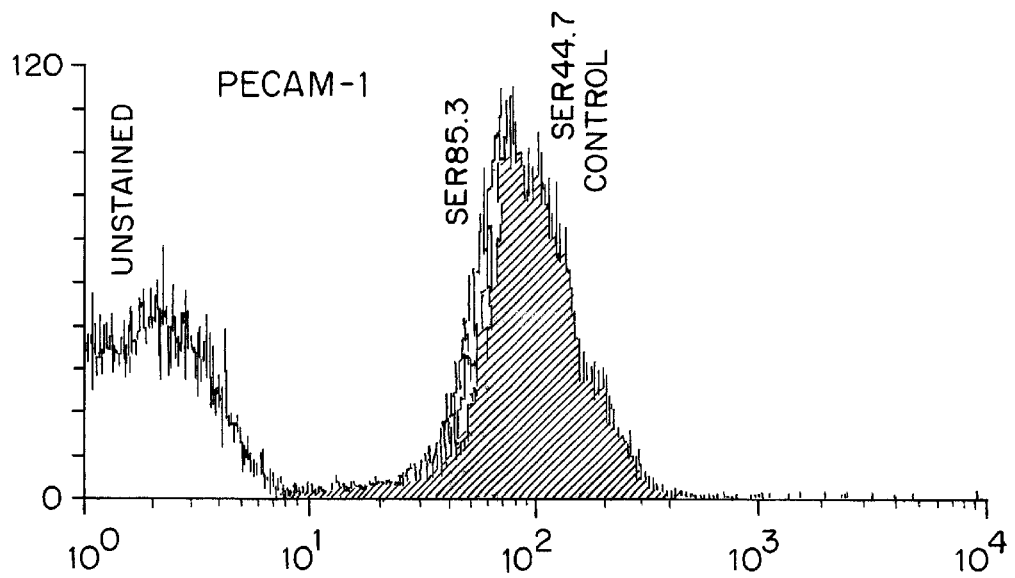

FIG. 10 is a graph from a flow cytometer showing the level of PECAM-1 expression when subjected to a control, 44.7 ng/mL of sertraline, 85.3 ng/mL of sertraline or unstained cells.

Figure 11:
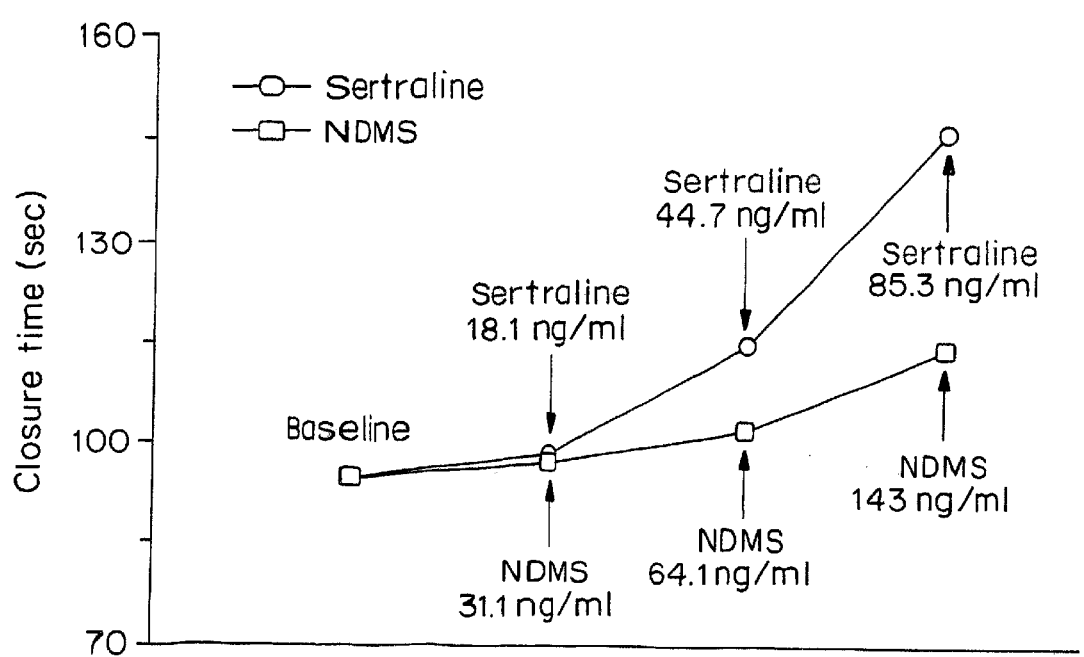

FIG. 11 is a graph showing the closure time with a collagen/ADP cartridge after whole blood incubation with sertraline at 18.1, 44.7 or 85.3 ng/ml; or N-desmethylsertraline (NDMS) at 31.1, 64.1, 143.0 ng/ml from a healthy volunteer.

DETAILED DESCRIPTION OF THE INVENTION

The present invention relates to methods for reducing the platelet activation state in an individual, and methods for treating or preventing a vascular condition by administering a serotonin inhibitor or antagonist (e.g., a SSRI).

Serotonin is present in areas of the body such as the gastrointestinal tract, the hypothalamus area of the brain and the retina. Compounds, referred to as selective Serotonin Reuptake Inhibitors (SSRIs), are used to treat various forms of depression, mood disorders, anxiety disorders or psychosomatic disorders. SSRIs enhance serotonergic neurotransmission by selectively inhibiting presynaptic neuronal uptake of serotonin, and thus, increasing serotonin concentrations at the synapses. Shelton, Richard C., *Clinical Therapeutics*, 16(5):768–782, 769 (1994). This mechanism is responsible for successful treatment of depression.

Serotonin is also found in platelets. Serotonin is stored in granules located in the platelets. Upon platelet activation, the granules release serotonin, thereby causing an increase of serotonin in the bloodstream. The present invention takes advantage of the surprising discovery that SSRIs are useful in inhibiting or reducing platelet activation.

Hence, the present invention relates to methods of reducing or inhibiting platelet activation by administering to an individual an effective amount of a SSRI. The terms, "a SSRI" and "a serotonin inhibitor or antagonist" refer to at least one (e.g., one or more) SSRI, or at least one serotonin inhibitor or antagonist, respectively. The platelet activation state refers to the occurrence of one or more of the following events: platelet aggregation, platelet adhesion, platelet agglutination, platelet release reactions (e.g., osteonectin, platelet factor 4 or β thrombomodulin), expression of platelet external receptors (e.g., GPIIb/IIIa or P-selectin), or platelet interaction with other blood components (e.g., collagen or fibrinogen) and cells (e.g., leukocytes). Administration of a SSRI decreases, reduces or inhibits one or more of these occurrences, thereby reducing the platelet activation state.

Several platelet activation markers exist which can be measured to assess the platelet activation state. Platelet activation can be assessed using platelet activation markers that are currently assessed in the art, as well as those that are later discovered. Examples of platelet activation markers are: CD9, GPIb, GPIIb, CDIa–IIa, P-selectin, PECAM-1, GPIIb/IIIa, vitronectin, integrins and adhesive molecules. A reduction in the platelet activation state also refers to a decrease in or an absence of one or more platelet activation markers. One or more platelet activation markers is decreased by at least about 10% (e.g., 20%, 30%, 40%, 50%, 60%, 70%, 80%, or 90), as compared to the level just prior to administration. Hence, one can measure the presence, absence or level of one or more platelet activation markers, and compare the result against a control. For example, one can obtain a suitable sample and compare the level of one or more platelet activation markers from previous time points (e.g., prior to administration of the SSRI or during the onset of a vascular event, disease or disorder). The level of one or more platelet activation markers decreases after administration of the SSRI, as compared to the level during the onset of the vascular event. One can also measure platelet activation markers in an individual prior to the onset of a vascular event (e.g., in a resting state or during a check-up), and determine the individuals baseline. Accordingly, administration of a SSRI after the onset of a vascular disease decreases the levels of one or more platelet activation markers, as compared to those levels during the onset of the vascular disease.

The level of platelet activation markers assessed can also be compared to a standard or control obtained from normal individuals. In one example, levels of platelet activation markers can be assessed in a population of healthy individuals or individuals who have not had a vascular event, disease or disorder. Such levels are referred to as a "negative control." Conversely, platelet activation marker levels can also be obtained from a pool of individuals who are undergoing a vascular event, disease or disorder, e.g., a "positive control." After administration of a SSRI, the level of one or more platelet activation markers decreases; the platelet activation marker level gets closer to the level of the negative control, and farther from the positive control. The level of a platelet activation marker decreases as compared to the level the platelet activation marker during the onset of the vascular event, disease or disorder. Hence, the methods include reducing the platelet activation state, or inhibiting platelet activation with administration of a SSRI, wherein one or more platelet activation markers is reduced or decreased, as compared to those levels during the occurrence of the vascular event, disease or disorder, or immediately prior to the administration of a SSRI.

In another embodiment, the present invention relates preventing the onset of a vascular event, disease or disorder. An effective amount of at least one SSRI can be administered to prevent the platelet activation state from increasing, or lessen the platelet activation state that would otherwise become active without SSRI administration. For example, an individual who is a risk for a vascular event, disease or condition can take a SSRI on a daily basis (or every other day), to prevent the platelet activation state from increasing as compared to a control or baseline. Baseline levels of the platelet activation state can be obtained prior to and/or during the course of administration of a SSRI. The platelet activation state, as measured by platelet markers can stay the same, or can even decrease. Similarly, the platelet activation marker level can be compared to a negative or positive control, wherein upon administration of SSRI, the levels are closer to the negative control, than the positive control. However measured, the platelet activation state is prevented from increasing, thereby preventing the occurrence of a vascular event, disease or disorder.

The present invention also relates to reducing or inhibiting platelet activation by contacting the platelets with a SSRI or metabolite thereof. This embodiment of the invention can be carried out in vivo or in vitro. The method reduces the level of one or more platelet activation markers, as compared to the level prior to contact of the SSRI with the platelets.

A serotonin antagonist or inhibitor is a composition that inhibits the binding of serotonin to another molecule; decreases or affects the function of serotonin; or reduces the secretion of serotonin from the platelets. In particular, a serotonin antagonist or inhibitor includes SSRIs. A SSRI reduces the secretion of serotonin from platelets. The SSRI not only reduces platelet aggregation, but surprisingly deactivates the platelets. Examples of SSRIs are sertraline (e.g., sertraline hydrochloride, marketed under the trademark "Zoloft®" by Pfizer, Inc.) or sertraline metabolite, fluvoxamine (e.g., fluvoxamine melate, marketed under the trademark "Luvox®" by Solvay Pharmaceuticals, Inc.), paroxetine (e.g., paroxetine hydrochloride, marketed under the trademark "Paxil®" by SmithKline Beecham Pharmaceuticals, Inc.) and fluoxetine (e.g., fluoxetine hydrochloride, marketed under the trademark "Prozac®" by Eli Lilly and Company) and citalopram (e.g., citalopram hydrobromide, marketed under the trademark "Celexa®" by Forest Laboratories, Parke-Davis, Inc.), and metabolites thereof. The present invention encompasses SSRIs that are currently used, or those later discovered or formulated.

The present invention encompasses metabolites of SSRIs, and therefore, the terms "SSRI" or "Selective Serotonin Reuptake Inhibitor" refer to the metabolite of the SSRI as well as the SSRI itself. SSRIs include biologically active portions, groups or fragments of the SSRI that can reduce the platelet activation state through modulation of the serotonin secretion or uptake.

It is believed that SSRIs inhibit 5-HT (5-hydroxytryptamine), a precursor to serotonin. Sertraline's chemical name is 1S, 4S-N-methyl-4-)3,4-dichlorophenyl)-1,2,3,4-tetrahydro-1-naphthylamine. Methods of making sertraline and its properties are described in U.S. Pat. Nos. 4,536,518; 4,940,731; 4,962,128; 5,130,338 and 5,248,699.

SSRI metabolites are active in reducing the platelet activation state. Sertraline's major liver metabolite is desmethylsertraline (NDMS), a product of sertraline demethylation. NDMS was previously thought to be clinically inactive. Surprisingly, NDMS significantly reduces the platelet activation state of platelets, as well as sertraline, and is active. sertraline is 98% protein-bound, and thus may alter serum levels of other highly protein-bound medications, such as warfarin and phenytoin. Sertraline is slowly absorbed after oral administration, with peak concentrations achieved approximately 4.5 to 8.5 hours after dosage of 50 to 200 mg. A half life of approximately 25–32 hours allows convenient once-a-day administration.

The prolonged half-life of the compound in combination with the existence of an inactive metabolite allows rapid equilibration of sertraline serum levels within approximately one week, and also results in fairly fast clearance of the medication following discontinuation of therapy. Sertraline is specific for the inhibition of serotonin reuptake and less potent for dopamine and norepinephrine blockade in comparison to other SSRI's. The pharmacokinetics and pharmacodynamics of sertraline are favorable. Single doses of sertraline in volunteers caused changes in the quantitative pharmaco-electroencephalogram suggesting antidepressant and anxiolytic actions, with sedative potential evident only at doses of 200 mg/daily or more.

Methods of making other SSRIs are also known in the art. Methods of making paroxetine and various forms of paroxetine are described in the art and in the following U.S. Pat. Nos. 5,872,132, 5,856,493, 5,811,436, 5,672,612, 4,721,723, 5,258,517. Methods and forms for making fluoxetine are also known in the art and described in U.S. Pat. Nos. 5,830,500, 5,760,243, 5,747,068, 5,708,035, 5,225,585. WO98/19513, WO98/19512 and WO98/19511 describe methods for preparing citalopram.

The present invention pertains to methods for preventing or treating an individual at risk for a vascular event, disease or disorder. Platelet activation is the cause or a significant contributor of several vascular diseases. Prevention of a vascular event, disease or disorder (e.g., vascular condition) refers to delaying or suppressing the onset of the vascular condition, or one or more of its symptoms. To treat an individual at risk for a vascular condition means to alleviate or ameliorate one or more of its symptoms. An individual at risk for a vascular condition refers to an individual with a history of vascular disease, an individual experiencing symptoms or risk factors (e.g., gender, weight) associated with or caused by the vascular condition, an individual undergoing a vascular procedure, or an individual who has tested positive for a vascular condition using a diagnostic test (e.g., electrocardiogram, cardiac catheterization, stress test, ultrasound poppler techniques). A vascular condition is a event, disease or disorder that involves a thrombosis or a narrowing of a blood vessel. Vascular events, diseases or disorders include cardiovascular diseases (e.g., coronary heart disease, myocardial infarction, angina or a disease in which a narrowing of a blood vessel occurs in at least one major artery), cerebrovascular diseases (e.g., stroke or transient ischemic attacks), vascular procedures (e.g., thrombotic re-occlusion subsequent to a coronary intervention procedure, heart or vascular surgery) or any other thrombotic event (e.g., pulmonary embolism, deep vein thrombosis or peripheral vascular thrombosis). Vascular conditions also include Syndrome X, which is a disease that is associated with unidentified chest pain.

One embodiment of the invention is a method for preventing or treating an individual at risk for a vascular condition, or a method for reducing the platelet activation state, by administering a SSRI along with at least one other compound or composition that is used for treating the vascular condition (a "vascular treating compound"). For an individual with a cardiovascular disease, the SSRI can be administered together with aspirin, heparin, an ADP inhibitor or antagonist (e.g., thienopyridine, such as ticlopidine hydrochloride (marketed under the trademark "Ticlid®" from Roche Laboratories) or clopidogrel bisulfate (marketed under the trademark "Pravix®" from Bristol-Myers Squibb and Sanofi), GPIIb/IIIa inhibitors (marketed under the trademark "ReoPro®" from Centocor, Inc.) or another SSRI. Individuals with cerebrovascular diseases can receive a SSRI together with Ticlid®, Pravix® or aspirin.

Mode and Manner of Administration

The SSRIs used in the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, ($17^{th}$ Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include, potassium sorbate, sodium metabisulfite, methyl paraben, propyl paraben, thimerosal, etc. The compositions can also be combined where desired with other active substances, e.g., enzyme inhibitors, to reduce metabolic degradation. A carrier (e.g., a pharmaceutically acceptable carrier) is preferred, but not necessary to administer the compound.

The SSRI can be a liquid solution, suspension, emulsion, tablet, pill, capsule, sustained release formulation, or powder. The method of administration can dictate how the composition will be formulated. For example, the composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The SSRIs used in the invention can be administered intravenously, parenterally, intramuscular, subcutaneously, orally, nasally, topically, by inhalation, by implant, by injection, or by suppository. The composition can be administered in a single dose or in more than one dose over a period of time to confer the desired effect. In one embodiment, sertraline, fluvoxamine, paroxetine, citalopram or fluoxetine can be administered orally in an amount between about 10 mg–2500 mg/daily. In particular, sertraline can be administered at about 25–200 mg/day, fluvoxamine at about 100–300 mg/day, fluoxetine at about 20–80 mg/day, paroxetine at about 20–50 mg/day and citalopram at about 20–40 mg/day.

The actual effective amounts of compound or drug can vary according to the specific composition being utilized, the mode of administration and the age, weight and condition of the patient. For example, as used herein, an effective amount of the drug is an amount which reduces the platelet activation state. Dosages for a particular individual patient can be determined by one of ordinary skill in the art using conventional considerations, (e.g. by means of an appropriate, conventional pharmacological protocol).

For enteral or mucosal application (including via oral and nasal mucosa), particularly suitable are tablets, liquids, drops, suppositories or capsules. A syrup, elixir or the like can be used wherein a sweetened vehicle is employed. Liposomes, microspheres, and microcapsules are available and can be used.

Pulmonary administration can be accomplished, for example, using any of various delivery devices known in the art such as an inhaler. See. e.g. S. P. Newman (1984) in *Aerosols and the Lung,* Clarke and Davis (eds.), Butterworths, London, England, pp. 197–224; PCT Publication No. WO 92/16192; PCT Publication No. WO 91/08760.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

The administration of the SSRI and the vascular treating compound can occur simultaneously or sequentially in time. The vascular treating compound can be administered before, after or at the same time as the SSRI. Thus, the term "co-administration" is used herein to mean that the SSRI and the vascular treating compound will be administered at times to achieve a reduction of the platelet activation state. The methods of the present invention are not limited to the sequence in which the SSRI and vascular treating compound are administered, so long as the vascular treating compound is administered close enough in time to produce the desired effect of reducing the platelet activation state.

Immunological Assessment of Platelet Activation Markers

Several suitable assays to measure soluble and/or membrane bound platelet activation markers (PAMs). Suitable assays encompass immunological methods, such as radioimmunoassay, flow cytometry, enzyme-linked immunosorbent assays (ELISA), chemiluminescence assays, and assessment with a volumetric capillary cytometry system. Any method known or developed later can be used for measuring PAMs.

The assays utilize antibodies reactive with a PAM, portions thereof or functional fragments thereof. The terms polyclonal and monoclonal refer to the degree of homogeneity of an antibody preparation, and are not intended to be limited to particular methods of production.

In several of the embodiments, immunological techniques detect PAM levels by means of an anti-PAM antibody (i.e., one or more antibodies). The term "anti-PAM antibody" includes monoclonal antibodies polyclonal antibodies, and/ or mixtures thereof. For example, these immunological techniques can utilize mixtures or a cocktail of polyclonal and/or monoclonal antibodies.

Anti-PAM antibodies can be raised against an appropriate immunogen, such as isolated and/or recombinant PAM or portion thereof (including synthetic molecules, such as synthetic peptides). One can also raise antibodies against a host cell which expresses a recombinant PAM. Additionally, cells expressing a recombinant PAM, such as transfected cells, can be used as immunogens or in a screen for antibody which binds receptor.

Techniques known in the art can be employed to prepare an immunizing antigen and to produce polyclonal or monoclonal antibodies. The art contains a variety of these methods (see e.g., Kohler et al., *Nature,* 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP210, with antibody producing cells can produce a hybridoma. Animals immunized with the antigen of interest and, preferably, an adjuvant provide the antibody producing cell (cells from the spleen or lymph nodes). Selective culture conditions isolate antibody producing hybridoma cells while limiting dilution techniques produce them. One can use suitable assays such as ELISA to select antibody producing cells with the desired specificity.

Other suitable methods can be employed to produce or isolate antibodies of the requisite specificity. Examples of other methods include selecting recombinant antibody from a library or relying upon immunization of transgenic animals such as mice which are capable of producing a full repertoire of human antibodies (see e.g., Jakobovits et al., *Proc. Natl. Acad. Sci. USA,* 90: 2551–2555 (1993); Jakobovits et al., *Nature,* 362: 255–258 (1993); Lonberg et al., U.S. Pat. No. 5,545,806; Surani et al., U.S. Pat. No. 5,545,807).

Immunological assays or techniques can be employed to determine the presence, absence or level of PAM in a biological sample. In determining the amounts of a membrane bound and/or soluble PAM, an assay generally includes combining the sample to be tested with an antibody having specificity for the PAM, under conditions suitable for formation of a complex between antibody and the PAM, and detecting or measuring (directly or indirectly) the formation of a complex.

A sample can be obtained and prepared by a method suitable for the particular sample (e.g., whole blood, platelet rich plasma, platelet poor plasma, serum), and select the assay format. For example, suitable methods for whole blood collection are venipuncture or obtaining blood from an in-dwelling arterial line. The container into which one deposits the blood can contain an anti-coagulant such as CACD-A, heparin, or EDTA.

One or more PAMs can be measured in a sample with or without platelets. To measure a soluble form of a PAM, the platelets are removed from the sample. A sample (e.g., blood) is collected, and platelets are removed (partially or completely) from the sample, for example, by preparation of serum or plasma (e.g., isolation of platelet poor plasma). Samples are processed to remove platelets within a time suitable to reduce artificial increases in soluble PAM. Initiation of such processing within about one hour, and preferably immediately, is desirable. Samples can be further processed as appropriate (e.g., by dilution with assay buffer). Additionally, one can add a reagent which stabilizes and prevents in vitro platelet activation. Examples of these stabilizing reagents are apyrase and $PGE_1$.

Methods of combining sample and antibody, and methods of detecting complex formation are also selected to be compatible with the assay format. Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, CYS, APC, chemiluminescent labels such as luciferase, radioisotope labels such as $^{32}P$, $^{125}I$, $^{131}I$, enzyme labels such as horseradish peroxidase, and alkaline phosphatase, β-galactosidase, biotin, avidin, spin labels and the like. The detection of antibodies in a complex can also be done immunologically with a second antibody which is then detected.

Flow Cytometry

One method for assessing PAM levels is flow cytometry. Methods of flow cytometry for measuring platelets or PAM are known in the art. (Shattil, Sanford J, et al. "Detection of Activated Platelets in Whole Blood using Activation-Dependent Monoclonal Antibodies and Flow Cytometry," *Blood,* Vol. 70, No 1 (July), 1987: pp307–315; Scharf, Rudiger E., et al., "Activation of Platelets in Blood Perfusing Angioplasty-damaged Coronary Arteries, Flow Cytometric Detection," *Arteriosclerosis and Thrombosis,* Vol 12, No 12 (December), 1992: pp 1475–1487.

For example, an assessment of one or more PAMs can be done. A sample comprising platelets is obtained from an individual. The sample is contacted with an antibody having specificity for a PAM under conditions suitable for formation of a complex between an antibody and the PAM expressed. A fluorescent label is used to detect the complex formation, either directly or indirectly. The in vivo affect of a SSRI is assessed by obtaining samples at particular time points (e.g., a baseline, during a vascular event, after administration of a SSRI, etc.), as described herein, and measuring the presence, absence, or level one or more PAMs.

For ex vivo assessment of the SSRIs effect on a PAM, a level of a PAM can be assessed by flow cytometry by first obtaining a sample that comprises platelets and then contacting the sample with a platelet activation agonist, such as phorbol myristate acetate (PMA), ADP (adenosine diphosphate), thrombin, collagen, and/or TRAP (thrombin receptor activating peptide), under conditions suitable for activation of platelets in the sample. The sample is in contact with the agonist preferably for a period of time effective to maximally activate the platelets. The sample is then subjected to a SSRI at particular concentrations (e.g., sertraline at 18.1, 44.7 or 85.3 ng/ml; NDMS at 31.1, 64.1 or 143 ng./ml). Then one contacts or stains the samples with a composition that comprises an anti-PAM antibody e.g., having a fluorescent label, preferably in an amount in excess of that required to bind the PAM expressed on the platelets, under conditions suitable for the formation of labeled complexes between the anti-PAM antibody and activated platelets. Then the formation of the complex in the sample is determined (detected or measured).

The sample can be divided to form controls. For example, a portion of the sample can be maximally activated and not contacted with a SSRI. Also, one can obtain a portion of the sample and not expose it to a platelet activation agonist, nor the SSRI to determine a baseline level of the PAM. See Example 2 for detailed description of the flow cytometry methods. This ex vivo method is not limited to flow cytometry, but can also be used in other methods for assessing PAM levels.

Radioimmunoassay

In addition to using flow cytometry to measure a PAM, a radioimmunoassay can be employed. A PAM can be assessed by a radioimmunoassay by first obtaining a suitable sample to be tested. The sample is contacted with an anti-PAM antibody (e.g., an anti-PAM antibody comprising a radioactive label, or an anti-PAM antibody comprising a binding site for a second antibody that has a radioactive label) preferably in an amount in excess of that required to bind the PAM expressed on the platelets, and under conditions suitable for the formation of labeled complexes between the anti-PAM antibody and activated platelets. The formation of the complex in the samples is determined by detecting or measuring the radioactivity in the sample.

Enzyme-Linked Immunosorbent Assays (ELISA)

Detection of a PAM in a suitable sample can also occur by employing ELISA methods. To determine a measurement of a PAM using an ELISA assay in a suitable sample, one contacts the sample with an anti-PAM antibody, and then measures the formation of a complex between the anti-PAM antibody and the PAM in the sample. The PAM can be measured by direct, indirect, sandwich or competitive ELISA formats. An antibody can be conjugated with labels such as biotin and HRP-streptavidin.

A solid support, such as a microtiter plate, dipstick, bead, or other suitable support, can be coated directly or indirectly with an anti-PAM antibody. For example, an anti-PAM antibody can coat a microtiter well, or a biotinylated anti-PAM Mab can be added to a streptavidin coated support. A variety of immobilizing or coating methods as well as a number of solid supports can be used, and can be selected according to the desired format.

In one embodiment, the sample or PAM standard is combined with the solid support simultaneously with the detector antibody. Optionally, this composition can be combined with a one or more reagents by which detection is monitored. For example, the sample such as PPP can be combined with the solid support simultaneously with (a) HRP-conjugated anti-PAM Mab, or (b) a biotinylated anti-PAM Mab and HRP-streptavidin.

A known amount of the PAM standard can be prepared and processed as described above for a suitable sample. This PAM standard assists in quantifying the amount of PAM detected by comparing the level of PAM in the sample relative to that in the standard.

A physician, technician, apparatus or a qualified person can compare the amount of detected complex with a suitable control to determine if the levels are decreased. For example, the level of a PAM following a vascular intervention procedure can be compared with a basal level for the individual, such as a level determined prior to or at the time of the procedure, or with levels in normal individuals or suitable controls, as described herein.

A variety of methods can determine the amount of PAM in complexes. For example, when HRP is used as a label, a suitable substrate such as OPD can be added to produce color intensity directly proportional to the bound anti-PAM Mab (assessed e.g., by optical density), and therefore to the PAM in the sample. One can compare the results to a suitable control such as a standard, levels of PAM in normal individuals, and baseline levels of PAM in a sample from the same donor. For example, the assay can be performed using a known amount of a PAM standard in lieu of a sample, and a standard curve established. One can relatively compare known amounts of the a PAM standard to the amount of complex formed or detected.

PAMs can be assessed using methods in the art or methods later developed in the future.

The following examples are meant to be illustrative and not limiting in any way.

EXEMPLIFICATION

Example 1

Design of Platelet Study

The Study is comprised of the following tasks:

Task A: In vitro experiments treating human blood with the optimal therapeutic concentrations of sertraline and metabolite were performed. The following groups of patients were studied in vitro using sertraline (18.1 ng/ml, 44.7 ng/ml) and N-desmethylsertraline (31.1 ng/ml, 64.1 ng/ml, 143 ng/ml):
1. Healthy volunteers (n=10)
2. Patients with major depression (n=10)
3. Patients with acute coronary syndrome (AMI and U/A; n=10)
4. Patients with stable ischemic heart disease and hypertension (n=10)
5. Patients with congestive heart failure (n=10)

Task B: Dose-dependency of platelet inhibition for mega doses (500 mg, 1 g, and 2 g) of sertraline and metabolite were established.

Task C: Platelet-related effects of sertraline and metabolite can be compared with those of the leading anti-platelet agents. A pilot crossover blinded study that assesses ex vivo effects of sertraline (50–100–200 mg) versus aspirin, clopidogrel and ticlopidine on platelet function can be conducted.

Trial Design for Task C

A Randomized Blind Crossover Study of Zoloft versus Aspirin, Plavix and Ticlid on Platelet Activity in Human Volunteers: Protocol SCRR 98-074.

The effects of three therapeutic doses of sertraline (50–100–200 mg/daily) is compared with aspirin (325 mg/daily), clopidogrel (75 mg/daily), and ticlopidine (150 mg/daily) on platelet activity.

Study Design

This study is a prospective, single-center, randomized, blinded, pilot crossover trial consisting of 3 parallel groups of 10 subjects each. Group one is treated with Zoloft® (50 mg/once daily) for 30 days. After 10 days (washout period) the same patients will receive aspirin (325 mg/once daily) for 30 days. The second group receive Zoloft® (100 mg/once daily) for 30 days. After 10 days (washout period) the same subjects receive Plavix (clopidogrel, 75 mg/once daily) for 30 days. The third group is treated with the highest dose of Zoloft® (150 mg/once daily) for 30 days. After 10 days (washout period) those subjects receive ticlopidine (150 mg/once daily) for 30 days.

Study Population

The population of the study contains 30 healthy subjects during chronic sertraline-aspirin, clopidogrel, and ticlopidine administration. Participants are divided in to 3 parallel groups of 10 individuals each.

The inclusion criteria are: 1. healthy subjects $\geq 18$ years of age and 2. signed Informed Consent form. The exclusion criteria are: 1. history of bleeding diathesis, 2. severe hypertension [systolic blood pressure >200 mm Hg or diastolic blood pressure >100 mm Hg on therapy], 3. major surgery within six weeks of enrollment, 3. history of stroke, other known central nervous system damage or structural abnormalities of the central nervous system, 4. drug or alcohol abuse, 5. pregnancy, 4. history of gastrointestinal bleeding (hematemesis, hematochezia, or melena or genitourinary bleeding (gross) within the past 30 days, 5. baseline PT is greater than 1.5 times control, platelet count <100, 000; baseline hematocrit <25%; or serum creatinine level >2.0 mg/dL, and 6. individuals who participated in other investigational drug studies within five weeks prior to study enrollment.

Example 2

Methods for Obtaining Samples and Measuring Platelet Aggregation and Platelet Activation Markers Sample Blood Draws Blood drawing was performed six times for each subject enrolled in the study.
1. Before Zoloft® treatment (baseline).
2. After 15 days of the initiation of Zoloft® therapy.
3. After 30 days of Zoloft® treatment.
4. After 10 days of washout period.

5. After 15 days of the initiation of aspirin/ Plavix®/or Ticlid® therapy.
6. After 30 days of the second drug administration.

Methods

The procedures for blood sampling and the analyses are listed below. Blood samples are collected from an antecubital vein via a 19-gauge needle into two plastic tubes. Each sample of free flowing blood will be collected through a fresh venipuncture site distal to any intravenous catheters using a needle and Vacutainer hood into 7 cc Vacutainer tubes (one with C.T.A.D., and the other with 3.8% trisodium citrate). If blood is collected simultaneously for any other studies, it is preferable that the platelet sample be obtained second or third, but not first. If only the platelet sample is collected, discharge the initial 2–3 cc of blood, and only then fill the vacutainer tube. The venipuncture is adequate if the tube fills within 15 seconds. All collections are performed by trained personnel.

Sample Processing

After the blood samples had been collected into two Vacutainer tubes, they were immediately, but gently, inverted 3 to 5 times to ensure complete mixing of the anticoagulant. Tubes are not shaken. The Vacutainer are filled to capacity, since excess anticoagulant can alter platelet function. Attention is paid to minimizing turbulence whenever possible. Small steps, such as slanting the needle in the Vacutainer to have the blood run down the side of tube instead of shooting all the way to the bottom, can result in significant improvement. These tubes are kept at room temperature and transferred directly to the laboratory personnel responsible for preparing the samples. The Vacutainer tubes are not chilled at any time.

Measurement of Platelet Aggregation

Trisodium citrate (3.8%) and whole blood is immediately mixed in a 1:9 ratio, and then centrifuged at 1200 g for 2.5 minutes, to obtain platelet-rich plasma (PRP), which is kept at room temperature for use within 1 hour for platelet aggregation studies. Platelet count is determined in each PRP sample with a Coulter Counter ZM (Coulter Co., Hialeah, Fla.). Platelet numbers are adjusted to $3.50 \times 10^8$/ml for aggregation with homologous platelet-poor plasma. PRP and whole blood aggregation tests are performed simultaneously. Whole blood is diluted 1:1 with the 0.5 ml PBS, and then swirled gently to mix. The cuvette with the stirring bar is placed in the incubation well and allowed to warm to 37° C. for 5 minutes. Then the sample are transferred to the assay well. An electrode is placed in the sample cuvette. Platelet aggregation is stimulated with 5 $\mu$M ADP, 1 $\mu$g/ml collagen, and 0.75 mM arachidonic acid. All agonists are obtained from Chronolog Corporation (Hawertown, Pa.). Platelet aggregation studies are performed using a Chrono-Log Whole Blood Lumi-Aggregometer (model 560-Ca). Platelet aggregability are expressed as the percentage of light transmittance change from baseline using platelet-poor plasma as a reference at the end of recording time for plasma samples, or as a change in electrical impedance for whole blood samples. Aggregation curves are recorded for 4 minutes and analyzed according to internationally established standards using Aggrolink® software.

Washed Platelets Flow Cytometry

Venous blood (8 ml) was collected in a plastic tube containing 2 ml of acid-citrate-dextrose (ACD) (7.3 g citric acid, 22.0 g sodium citrate×2H2O and 24.5 glucose in 1000 ml distilled water) and mixed well. The blood-ACD mixture was centrifuged at 1000 r.p.m. for 10 minutes at room temperature. The upper $\frac{2}{3}$ of the platelet-rich plasma (PRP) was then collected and adjusted to pH=6.5 by adding ACD. The PRP was then centrifuged at 3000 r.p.m. for 10 minutes. The supernatant was removed and the platelet pellet was gently resuspended in 4 cc of the washing buffer (10 mM Tris/HCl, 0.15 M NaCl, 20 mM EDTA, pH=7.4). Platelets were washed in the washing buffer, and in TBS (10 mM Tris, 0.15 M NaCl, pH=7.4). All cells were then divided into ten plastic capped tubes. Nine portions of washed platelets were incubated with 5 $\mu$l fluorescein isothiocyanate (FITC)-conjugated antibodies in the dark at +4° C. for 30 minutes, and one part remained unstained and served as a negative control. Surface antigen expression was measured with monoclonal murine anti-human antibodies: CD9 (p24); CD41a (IIb/IIIa, aIIbb3); CD42b (Ib); CD61(IIIa) (DAKO Corporation, Carpinteria, Calif.); CD49b (VLA-2, or a2b1); CD62p (P-selectin); CD31 (PECAM-1); CD 41b (IIb); and CD51/CD61 (vitronectin receptor, avb3) (PharMingen, San Diego Calif.). After incubation, the cells were washed with TBS and resuspended in 0.25 ml of 1% paraformaldehyde. Samples were stored in the refrigerator at +4° C., and analyzed on a Becton Dickinson FACScan flow cytometer with laser output of 15 mw, excitation at 488 nm, and emission detection at 530±30 nm. The instrument was calibrated daily with fluorescence beads (CaliBRITE; Becton Dickinson) and measured FITC-conjugated fluorescence intensity. All parameters were obtained using four decade logarithmic amplification. The data was collected and stored in list mode, and then analyzed using CELLQuest® (version 1.2.2) software. Procedures are described in detail in (Gurbel, P. A. et al., J Amer Coll Cardiol 31: 1466–1473 (1998); Serebruany, V. L. et al., *Am Heart J* 136: 398–405 (1998); Gurbel, P. A. et al., *Coron Artery Dis* 9: 451–456 (1998) and Serebruany, V. L. et al., *Arterioscl Thromb Vasc Biol* 19: 153–158 (1999)).

Whole Blood Flow Cytometry

Four cc of blood was collected in a tube, containing 2 cc of acid-citrate-dextrose (ACD) (7.3 g citric acid, 22.0 g sodium citrate×2H2O and 24.5 glucose in a total amount of 1000 mL distilled water) and mixed well. The buffer, TBS (10 mM Tris, 0.15 M NaCl, pH 7.4) and the following fluorescein isothiocyanate (FITC) conjugated monoclonal antibodies (PharMingen, San Diego, Calif., USA, and DAKO, Calif., USA) were removed from a refrigerator and allowed to warm at room temperature (RT): CD41 (IIb/IIIa), CD31 (PECAM-1), CD62p (P-selectin), CD51/61 (Vitronectin receptor). Six amber tubes (1.25 ml) were obtained and marked. One Eppendorf tube (1.5 ml) was labeled with "Dill WB", Patient ID #, Initial and Date. The amber tubes and Eppendorf tube were placed in the rack. 450 ml of TBS buffer was pipetted to the labeled Eppendorf tube. The patient's whole blood tube was inverted gently twice to mix. 50 $\mu$l of whole blood was pipetted to the "Dill WB" labeled Eppendorf tube. The Eppendorf tube was capped and the diluted whole blood was mixed by inverting the Eppendorf tube gently two times 50 $\mu$l of diluted whole blood was pipetted to each amber tube. 5 $\mu$l of appropriate antibody was pipetted to the bottom of the corresponding amber tube. The tubes were covered with aluminum foil and incubated at 4° C. for 30 minutes. After incubation, 400 $\mu$l of 2% buffered paraformaldehyde was added. To prepare 2% Paraformaldehyde: Dilute 1 part 10% paraformaldehyde with 4 parts TBS. This solution was stored at 4° C. for up to one week. The amber tubes were closed with a lid tightly and stored in a refrigerator at 4° C. until the flow cytometric analysis. The samples are analyzed on a Becton Dickinson FACScan flow cytometer. The instrument is set up to measure forward light scatter (FSC), and FITC fluorescence. All parameters are collected using four decade logarithmic amplification. These data are collected in list mode files and then analyzed.

Cartridge-Based Platelet Analyzers

A Platelet-Function Analyzer referred to as PFA-100® (Dade Behring, Deerfield, Ill.) was used. The PFA-100® is a high shear-inducing analyzer that simulates primary hemostasis after injury to a small vessel under flow conditions. The PFA-100® system measures the time required for a patient's blood sample to form a"platelet plug" in the first phase of blood clot formation. That time interval, which normally ranges from one to three minutes, is called "closure time." The device provides a constant negative pressure that aspirates whole blood which comes into contact with the collagen coated membrane and then passes through the aperture. The time required to obtain occlusion of the aperture is digitally recorded.

The PFA-100® system permits detection of platelet dysfunction during primary hemostasis, the first phase of hemostasis or coagulation. The system consists of a microprocessor-controlled instrument and disposable test cartridges that measure how well a patient's platelets adhere and aggregate to form a platelet plug.

Soluble P-selectin (Centocor, Inc., Malvern, Pa., USA); and PECAM-1 (Bender MedSystems, Vienna, Austria) are measured:

P-selectin, (CD 62p, GMP-140, PADGEM), is a 130 kD integral membrane glycoprotein, and a member of the selectin superfamily found on the surface of platelets and endothelial cells. As an alpha granule constituent, P-selectin is expressed on platelets that have undergone the release reaction. This receptor participates in leukocyte rolling on the endothelium, and is believed to be an indicator of cell activation. A soluble form of P-selectin is smaller than the platelet bound molecule, and is encoded by an alternatively spliced mRNA from which the exon containing transmembrane domain has been removed. In several animal models, administration of monoclonal antibodies against P-selectin resulted in a significant reduction in infarct size presumably via blockade of neutrophil accumulation in the myocardium.

Platelet/Endothelial Cell Adhesion Molecule-1 (PECAM-1 CD 31), a 130 kD integral membrane glycoprotein, and a member of immunoglobulin gene superfamily, is found on the surface of platelets and leukocytes, and at the intercellularjunctions of the endothelial cells. PECAM-1 is directly involved in the formation of the vascular bed, affects the up-regulation of integrin function on leukocytes, and has been implicated as a trigger that regulates leukocyte trafficking through the vessel wall. As an alpha granule constituent, PECAM-1 is a distinct, well-defined component of the platelet plasma membrane with the intracellular distribution identical to glycoprotein IIb/IIIa. Native resting human platelets express approximately eight thousand molecules per platelet, whereas thrombin-stimulated platelets exhibit nearly two fold expression.

A soluble form of PECAM-1, which is 5–10 kD smaller than platelet-associated PECAM-1, contains a cytoplasmic tail and is encoded by an alternatively spliced mRNA from which the exon containing transmembrane domain has been removed. In spite of the proposed importance of PECAM-1, little is known about its biosynthesis, processing and turnover on the cell surface. The administration of monoclonal antibodies against PECAM-1 also resulted in a significant reduction in infarct size presumably via blockade of neutrophil accumulation in the myocardium.

Plasma samples will be extracted with ethanol and then stored at −80° C. before final determination. Enzyme-linked immunosorbent assays will be used according standard techniques and as described herein.

Eicosanoids

The balance between arterial wall prostacyclin production and platelet thromboxane synthesis directly influences vasoreactivity and thrombosis. Support for the relevance of measuring prostanoids during coronary events was found in a study demonstrating that coronary arteries produce large amounts of prostacyclin compared to the production of low quantities of thromboxane. Prostacyclin and its analogs (e.g. defibrotide) were shown to reduce tissue injury during myocardial ischemia. Early studies have found that thromboxane does not appear to be a mediator of reversible ischemia-reperfusion damage. However, recent observations have described beneficial cardioprotective properties of thromboxane receptor blockade, or thromboxane synthetase inhibition on recovery after acute coronary events.

Under physiological conditions, eicosanolds have a very short half-life. Therefore, their metabolites are analyzed. Thromboxane B2 (TxB2), the stable breakdown product of thromboxane $A_2$, and 6keto-$PGF_{1alpha}$, the stable degradation product of prostacyclin, are measured in the platelet poor plasma (PPP), which are kept at −4° C. In vitro prostaglandin biosynthesis is inhibited with 7.5 mM EDTA and 4 ug/ml indomethacin. Plasma samples are extracted with ethanol and then stored at −80° C. before final prostaglandin determination, using TiterZymes® enzyme immunoassays according to standard techniques (PerSeptive Diagnostics, Inc., Cambridge, Mass., USA). The extract are evaporated under a vacuum and the residue are redissolved in an assay buffer.

Platelet factor 4, and B-thromboglobulin as established platelet-released compounds are measured in platelet poor plasma with the ASSERACHROM® ELISA kits. (Diagnostica Stago, Asnieres, France).

Closure Time Measured with the Dade Behring In vitro Platelet Function Analyzer, PFA-100™

An in vitro system for the detection of platelet dysfunction, PFA-100™, has been developed. It provides a quantitative measure of platelet function in anticoagulated whole blood. The system comprises a microprocessor-controlled instrument and a disposable test cartridge containing a biologically active membrane. The instrument aspirates a blood sample under constant vacuum from the sample reservoir through a capillary and a microscopic aperture cut into the membrane. The membrane is coated with collagen and epinephrine or adenosine 5'-diphosphate. The presence of these biochemical stimuli, and the high shear rates generated under the standardized flow conditions, result in platelet attachment, activation, and aggregation, slowly building a stable platelet plug at the aperture. The time required to obtain full occlusion of the aperture was reported as the "closure time." The PFA-100™ system has potential applications in routine evaluation of platelet function in the clinical setting because of its accuracy, ease of operation, and rapid turnaround of results.

The membrane in the PFA-100 test cartridge serve as a support matrix for the biological components and allows placement of the aperture. The membrane was a standard nitrocellulos filtration membrane with an average pore size of 0.45 $\mu$m. The blood entry side of the membrane was coated with 2 $\mu$g of fibrillar Type I equine tendon collagen and 10 $\mu$g of epinephrine bitartrate or 50 $\mu$g of adenosine 5'-diphosphate (ADP). These agents provide controlled stimulation to the platelets as the blood sample passes through the aperture. The collagen surface also served as a well-defined matrix for platelet deposition and attachment.

The principle of the PFA-100 test is very similar to that described by Kratzer and Born. Kratzer, et al., *Haemostasis*

15: 357–362 (1985). The test utilized whole blood samples collected in 3.8% of 3.2% sodium citrate antigcoagulant. The blood sample was aspirated through the capillary into the cup where it comes in contact with the coated membrane, and then passes through the aperture. In this complex flow system, the calculation of shear stresses at the aperture was not trivial. However, if a cylindrical geometry is assumed, then it can be shown that at normal blood viscosity of 0.0035 $N/m^2$, the platelets was subjected to a shear rate of 5000–6000 $second^{-1}$. In response to the stimulation by collagen and epinephrine or ADP present in the coating, and the shear stresses at the aperture, platelets adhered and aggregated on the collagen surface starting at the area surrounding the aperture. During the course of the measurement, a stable platelet plug formed that ultimately occluded the aperture. The time required to obtain full occlusion of the aperture is defined as the "closure time" and is indicative of the platelet function in the sample.

Statistical Analyses

The primary study outcome are Platelet inhibition [aggregability and major receptor expression] at 15 and 30 days after drug administration. Statistical analysis of parameters at each time point is performed in order to determine possible correlations between them. Such an approach allows us to define relevant anti-platelet properties of sertraline and its metabolite when compared with the leading oral anti-platelet agents.

The data in table 1 was obtained using the methods described herein, and in particular, in Examples 1 and 2. The levels of various PAMs were assess from samples of human volunteers. The samples (either PRP or Whole Blood (WB)) were incubated with sertraline at 18.1, 44.7 or 85.3 ng/ml; or N-desmethylsertraline (NDMS) at 31.1, 64.1, 143.0 ng/ml. Baseline levels of the PAMs were also obtained (without exposure to sertraline or NDMS). Several PAMs exhibited a decrease in their expression when exposed to either sertraline or its metabolite, NDMS. In particular, many of the PAMs showed a dose dependant response, wherein an increase in the concentration of either sertraline or NDMS resulted in a corresponding decrease in the PAM expression. These results are significant because they show that administration of a SSRI reduces the platelet activation state, in a dose dependant fashion.

TABLE 1

Expression of Major Platelet Antigens after Incubation of the Platelet Rich Plasma (Log Fluorescence Intensity) and Whole Blood (% of Cell Positivity for P-selectin) with the Therapeutic Concentrations of sertraline and Desmethylsertraline in Healthy, Human Volunteers:

| Receptor | Base-line | sertraline (ng/ml) | | | Desmethyl sertraline (ng/ml) | | |
|---|---|---|---|---|---|---|---|
| | | 18.1 | 44.7 | 85.3 | 31.1 | 64.2 | 143 |
| Platelet Rich Plasma | | | | | | | |
| CD9 (peak) | 897 | 938 | 777 | 716 | 620 | 805 | 770 |
| CD9 (mean) | 1068 | 948 | 905 | 742 | 728 | 859 | 837 |
| GP Ib (peak) | 281 | 125 | 74 | 67 | 94 | 266 | 336 |
| GP Ib (mean) | 300 | 139 | 97 | 65 | 146 | 299 | 309 |
| GP IIb (peak) | 45 | 26 | 35 | 22 | 31 | 31 | 35 |
| GP IIb (mean) | 47 | 31 | 31 | 30 | 33 | 37 | 30 |
| GP IIIa (peak) | 1197 | 1197 | 1084 | 704 | 913 | 1144 | 1046 |
| GP IIIa (mean) | 1438 | 1389 | 1197 | 816 | 981 | 1178 | 1182 |
| CPIa-IIa (peak) | 47 | 47 | 37 | 30 | 42 | 40 | 40 |
| CPIa-IIa (mean) | 57 | 51 | 49 | 35 | 41 | 42 | 43 |
| Vitronectin (peak) | 617 | 550 | 553 | 537 | 620 | 508 | 670 |
| Vitronectin (mean) | 476 | 810 | 510 | 667 | 677 | 623 | 732 |
| P-selectin (peak) | 333 | 335 | 297 | 273 | 459 | 494 | 398 |

TABLE 1-continued

Expression of Major Platelet Antigens after Incubation of the Platelet Rich Plasma (Log Fluorescence Intensity) and Whole Blood (% of Cell Positivity for P-selectin) with the Therapeutic Concentrations of sertraline and Desmethylsertraline in Healthy, Human Volunteers:

| Receptor | Base-line | sertraline (ng/ml) | | | Desmethyl sertraline (ng/ml) | | |
|---|---|---|---|---|---|---|---|
| | | 18.1 | 44.7 | 85.3 | 31.1 | 64.2 | 143 |
| P-selectin (mean) | 16 | 14 | 14 | 18.4 | 11.8 | 10.5 | 13.5 |
| PECAM-1 (peak) | 101 | 88 | 71 | 66 | 60 | 91 | 74 |
| P-selectin (mean) | 16 | 14 | 14 | 18.4 | 11.8 | 10.5 | 13.5 |
| PECAM-1 (peak) | 101 | 88 | 71 | 66 | 60 | 91 | 74 |
| PECAM-1 (mean) | 108 | 117 | 104 | 84 | 74 | 101 | 81 |
| GP IIb/IIIa (peak) | 805 | 991 | 518 | 421 | 457 | 649 | 509 |
| GP IIb/IIIa (mean) | 1106 | 1038 | 748 | 533 | 580 | 743 | 708 |
| Whole Blood | | | | | | | |
| GP IIb/IIIa (peak) | 537 | 418 | 437 | 437 | 340 | 355 | 264 |
| GP IIb/IIIa (mean) | 515 | 479 | 476 | 498 | 346 | 403 | 314 |
| P-Selectin (% +) | 7.4 | 7.7 | 4.4 | 6.9 | 1.2 | 3.3 | 0.4 |

Figure 1:
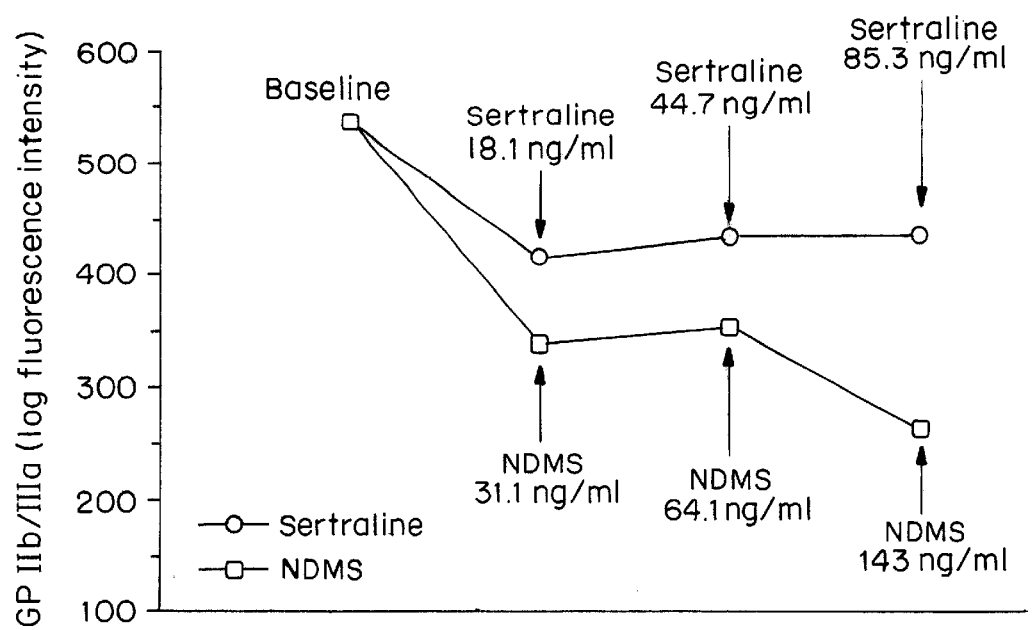
FIG. 1 is a graph showing the log fluorescence intensity of GPIIb/IIIa after incubation of whole blood with sertraline at 18.1, 44.7 or 85.3 ng/ml; or N-desmethylsertraline (NDMS) at 31.1, 64.1, 143.0 ng/ml from a healthy volunteer.

FIG. 1 illustrates the results from Table 1. FIG. 1 shows the GPIIb/IIIa expression after incubation of whole blood from a healthy volunteer with sertraline at 18.1, 44.7 or 85.3 ng/ml; or NDMS at 31.1, 64.1, 143.0 ng/ml. Both sertraline and NDMS caused a dose dependent decrease in the expression. The metabolite, NDMS, more effectively decreased the expression of GPIIb/IIIa.

Figure 2:
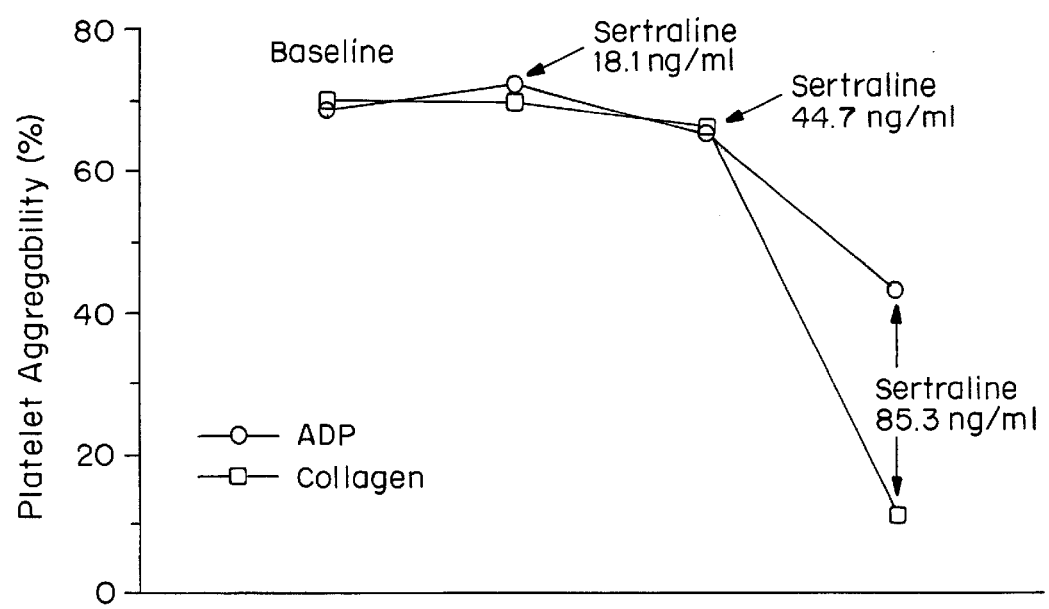
FIG. 2 is a graph illustrating the percent (%) of platelet aggregation induced either by adenosine diphosphate (ADP) or collagen in Platelet Rich Plasma (PRP) from a healthy volunteer incubated with sertraline at 18.1, 44.7 or 85.3 ng/ml.
Figure 3:
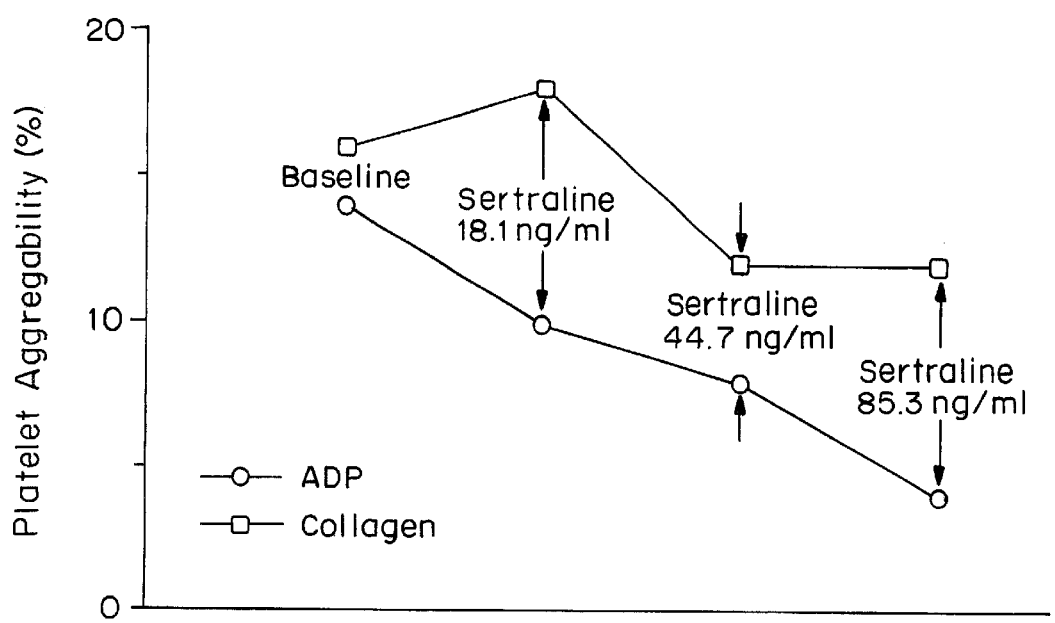
FIG. 3 is a graph illustrating the percent (%) of platelet aggregation induced either by adenosine diphosphate (ADP) or collagen in whole blood from a healthy volunteer incubated with sertraline at 18.1, 44.7 or 85.3 ng/ml.

FIGS. 2 and 3 show the percent of platelet aggregation of whole blood or PRP, respectively, after incubation with particular amounts of sertraline. The platelet aggregation was induced with either ADP or collagen. The data illustrate that the amount platelet aggregation decreases with increasing amounts of sertraline.

Table 2 show the expression of various PAMs in samples from post-angioplasty patients on aspirin. The samples were incubated with a series of concentrations: sertraline at 18.1, 44.7 or 85.3 ng/ml; or NDMS at 31.1, 64.1, 143.0 ng/ml. The levels of PAMs were measured in both PRP and WB using flow cytometric analysis, described herein and, in particular, in Example 2. As in Table 1, Table 2 shows a dose dependant decrease in several PAM levels when the samples are incubated with increasing concentrations of sertraline or NDMS. The decrease in expression of several PAMs indicate a significant reduction in the platelet activation state in samples from post-angioplasty patients.

TABLE 2

Expression of major platelet antigens after incubation of the platelet rich plasma (log fluorescence intensity) and whole blood (% of cell positivity for P-selectin) with the therapeutical concentrations of sertraline and desmethylsertraline in a post-angioplasty patient on aspirin:

| Receptor | Base-line | sertraline (ng/ml) | | | Desmethyl sertraline (ng/ml) | | |
|---|---|---|---|---|---|---|---|
| | | 18.1 | 44.7 | 85.3 | 31.1 | 64.2 | 143 |
| Platelet Rich Plasma | | | | | | | |
| CD9 (peak) | 835 | 1027 | 850 | 964 | 1046 | 930 | 850 |
| CD9 (mean) | 856 | 949 | 1015 | 984 | 908 | 927 | 853 |
| GP Ib (peak) | 302 | 305 | 257 | 186 | 165 | 167 | 201 |
| GP Ib (mean) | 313 | 324 | 220 | 182 | 167 | 198 | 222 |
| GP IIb (peak) | 24 | 29 | 31 | 34 | 21 | 20 | 25 |
| GP IIb (mean) | 29 | 30 | 27 | 37 | 24 | 22 | 29 |
| GP IIIa (peak) | 1027 | 1114 | 1370 | 1310 | 1298 | 1144 | 1219 |
| GP IIIa (mean) | 1149 | 1247 | 1404 | 1321 | 1235 | 1247 | 1259 |

TABLE 2-continued

Expression of major platelet antigens after incubation of the platelet rich plasma (log fluorescence intensity) and whole blood (% of cell positivity for P-selectin) with the therapeutical concentrations of sertraline and desmethylsertraline in a post-angioplasty patient on aspirin:

| Receptor | Base-line | sertraline (ng/ml) | | | Desmethyl sertraline (ng/ml) | | |
|---|---|---|---|---|---|---|---|
| | | 18.1 | 44.7 | 85.3 | 31.1 | 64.2 | 143 |
| CPIa-IIa (peak) | 53 | 55 | 60 | 60 | 59 | 53 | 48 |
| CPIa-IIa (mean) | 51 | 63 | 70 | 67 | 62 | 62 | 40 |
| Vitronectin (peak) | 785 | 515 | 393 | 585 | 560 | 425 | 544 |
| Vitronectin (mean) | 676 | 405 | 344 | 529 | 504 | 380 | 482 |
| P-selectin (peak) | 452 | 414 | 92 | 211 | 322 | 537 | 378 |
| P-sdechn (mean) | 14.4 | 15.1 | 20.9 | 27.9 | 15 | 11 | 13.4 |
| PECAM-1 (peak) | 74 | 76 | 98 | 93 | 83 | 84 | 84 |
| PECAM-1 (mean) | 82 | 94 | 99 | 97 | 94 | 105 | 90 |
| GP IIb/IIIa (peak) | 805 | 679 | 798 | 922 | 791 | 777 | 716 |
| GP IIb/IIIa (mean) | 1106 | 911 | 962 | 1035 | 948 | 918 | 836 |
| Whole Blood | | | | | | | |
| GP IIb/IIIa (peak) | 297 | 266 | 244 | 217 | 268 | 245 | 232 |
| GP IIb/IIIa (mean) | 286 | 252 | 230 | 198 | 277 | 219 | 242 |
| P-Selectin (% +) | 13.2 | 8.16 | 5.35 | 4.41 | 10.68 | 8.04 | 9.92 |

Figure 4:
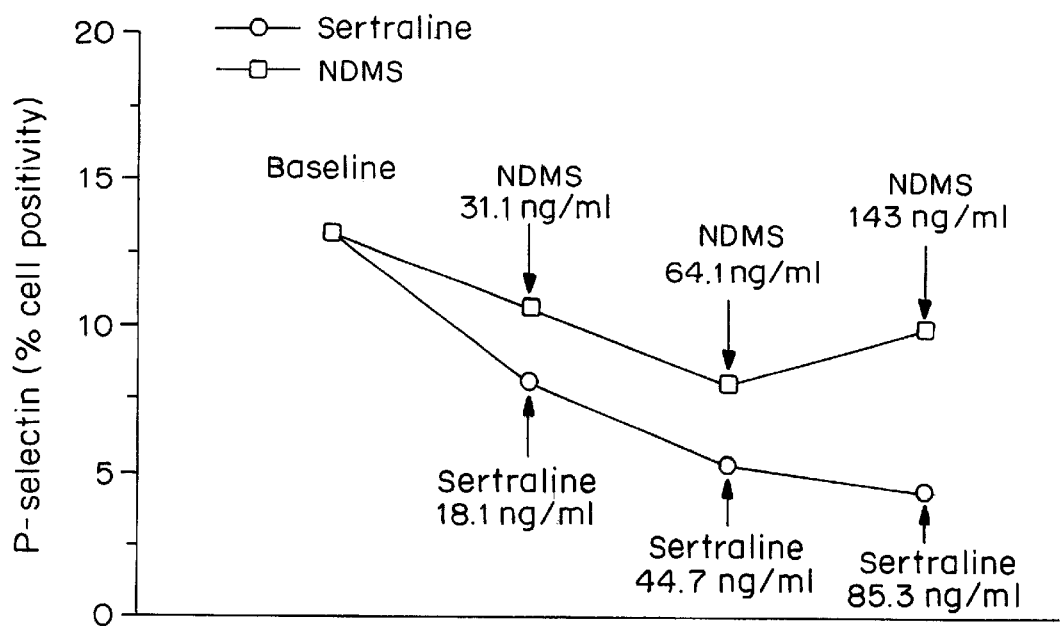
FIG. 4 is a graph showing the percent (%) cell positivity of P-Selectin after incubation of whole blood with sertraline at 18.1, 44.7 or 85.3 ng/ml; or N-desmethylsertraline (NDMS) at 31.1, 64.1, 143.0 ng/ml from a post-angioplasty patient.

FIGS. 4 and 7 show that P-selectin and GPIIb/IIIa expression in whole blood after incubation with either sertraline or NDMS at increasing concentrations resulted in striking decreases in expression. This decrease in expression indicates that the SSRI is actually deactivating the platelets, thereby resulting in decreased expression of these PAMs.

Figure 5:
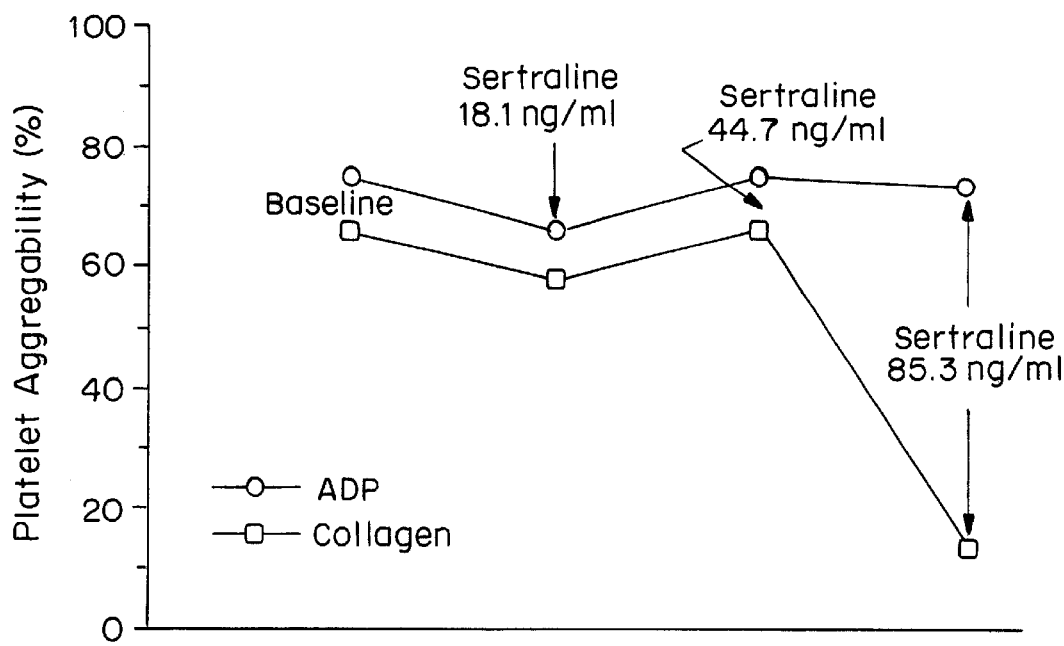
FIG. 5 is a graph illustrating the percent (%) of platelet aggregation induced either by adenosine diphosphate (ADP) or collagen in Platelet Rich Plasma (PRP) from a post-coronary angioplasty patient incubated with sertraline at 18.1, 44.7 or 85.3 ng/ml.
Figure 6:
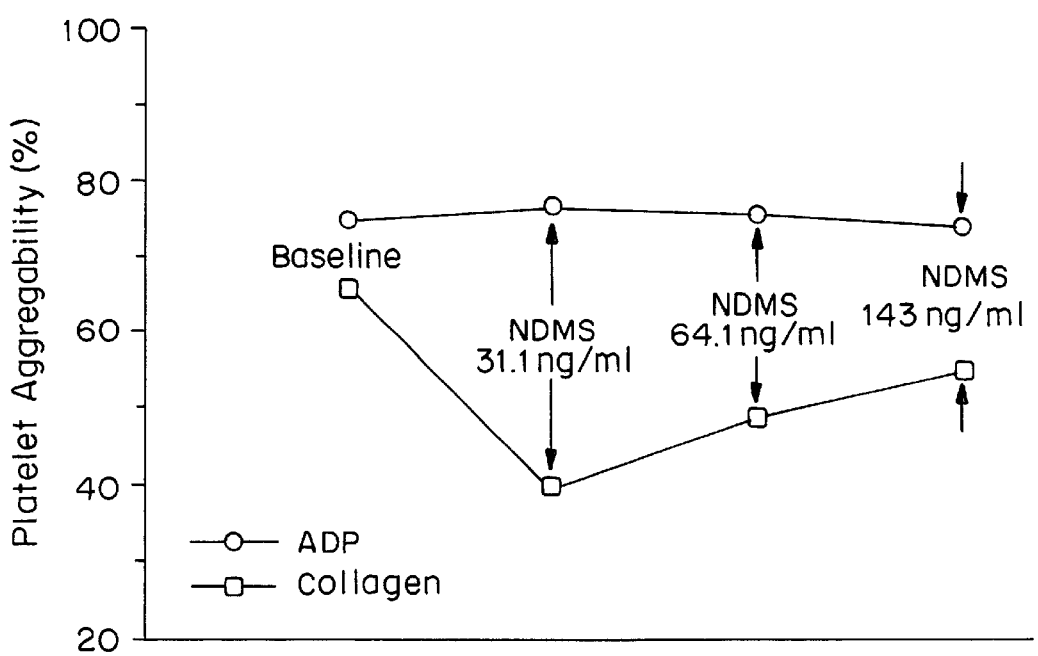
FIG. 6 is a graph illustrating the percent (%) of platelet aggregation induced either by adenosine diphosphate (ADP)

Similarly, FIGS. 5 and 6 show a decrease in platelet aggregation in PRP after incubation with either sertraline or NDMS. The samples were activated with either ADP or collagen, and then incubated with the specified concentrations of sertraline or NDMS. These graphs show that less platelets were activated and had the ability to aggregate when exposed to a SSRI.

FIGS. 8, 9 and 10 are flow cytometric graphs of GPIb, GP IIb/IIIa and PECAM-1, respectively, and clearly show a dose dependent decrease in the expression of the PAM with increasing amounts of sertraline.

FIG. 11 shows the closure time (the time for a platelet plug to form) when sertraline at 18.1, 44.7 or 85.3 ng/ml; or NDMS at 31.1, 64.1, 143.0 ng/ml is incubated with whole blood from a healthy volunteer. FIG. 11 shows a decrease in the time (seconds) for the platelets to form a platelet plug when increasing concentrations of sertraline or NDMS.

Together, these data show that a SSRI or its metabolite successfully reduces the platelet activation state and decrease the expression of various PAMs. The data indicate that sertraline hydrochloride (Zoloft®) has direct platelet inhibitory properties in humans. Moreover, N-desmethylsertraline, a stable final metabolite of sertraline which was previously considered inactive, surprisingly exhibited potent dose-dependent effects inhibiting human platelets in both platelet rich plasma and in the whole blood.

Example 3

Results of the Study

Sertraline is a universal platelet inhibitor in healthy controls, and patients with coronary artery disease, including those on aspirin:

A. Dose-dependent inhibition of ADP-, and collagen-induced platelet aggregation in plasma (in vitro).

B. Dose-dependent inhibition of ADP-, and collagen-induced platelet aggregation in whole blood (in vitro).

C. Incubation of platelets with sertraline (plasma concentration 85.3 ng/ml, which is equivalent to 200 mg/daily) is associated with diminished surface expression of major receptors including glycoprotein IIb/IIIa complex (GP IIb/IIIa), very late antigen-2 (VLA-2, or GPIb-IIa), GP Ib, CD9 (p24), vitronectin receptor, PECAM-1, and P-selectin.

Sertraline affects markers of endothelial and/or platelet activation in patients with depression following myocardial infarction:

A. Mild, but consistent reduction of the ex vivo PECAM-1 and P-selectin plasma levels after 16 weeks of the sertraline/placebo therapy.

B. Increased magnitude of standard error at 16 weeks of the sertraline/placebo therapy may be due to the differences between the treatment groups.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of reducing a platelet activation state of an individual comprising, administering to the individual an effective amount of at least one selective serotonin reuptake inhibitor (SSRI), wherein the SSRI prevents the reduction of serotonin in blood of the individual, and the SSRI is selected from the group consisting of sertraline, a sertraline metabolite, fluvoxamine, a fluvoxamine metabolite, paroxetine, a paroxetine metabolite, fluoxetine, and a fluoxetine metabolite.

2. The method of claim 1, wherein sertraline is administered orally, by injection, intravenously, intramuscularly, subcutaneously, parenterally, nasally, by inhalation, by implant, or by suppository.

3. The method of claim 1, wherein the SSRI is administered orally in an amount between about 10 mg–2500 mg/daily.

4. The method of claim 3, comprising comparing the level of at least one platelet activation marker from a sample taken from the individual to a control.

5. A method of preventing or treating an individual at risk for a vascular event, disease or disorder, comprising administering to the individual an effective amount of a SSRI, wherein the SSRI prevents the reduction of serotonin in blood of the individual, and the SSRI is selected from the group consisting of sertraline, a sertraline metabolite, fluvoxamine, a fluvoxamine metabolite, paroxetine, a paroxetine metabolite, fluoxetine, and a fluoxetine metabolite.

6. The method of claim 5, wherein the vascular event, disease or disorder is selected from a group consisting of: myocardial infarction, angina, stroke, pulmonary embolism, transient ischemic attack, deep vein thrombosis, thrombotic re-occlusion subsequent to a coronary intervention procedure, heart surgery or vascular surgery, peripheral vascular thrombosis, Syndrome X, heart failure, and a disorder in which a narrowing of at least one coronary artery occurs.

7. The method of claim 6, wherein sertraline is administered orally, by injection, intravenously, intramuscularly, subcutaneously, parenterally, nasally, by inhalation, by implant, or by suppository.

8. The method of claim 6, the SSRI is administered orally in an amount between about 10 mg–2500mg/daily.

9. The method of claim 8, comprising comparing the level of at least one platelet activation marker from a sample taken from the individual, to a control, wherein the level is decreased.

10. The method of claim 9, wherein the platelet activation marker is reduced by at least about 10%.

11. A method of treating an individual with coronary heart disease comprising administering a therapeutically effective amount of at least one SSRI in a carrier to the individual, wherein the SSRI prevents the reduction of serotonin in blood of the individual, the SSRI is selected from the group consisting of sertraline, a sertraline metabolite, fluvoxamine, a fluvoxamine metabolite, paroxetine, a paroxetine metabolite, fluoxetine, and a fluoxetine metabolite, and the platelet activation state of the individual decreases.

12. The method of claim 11, wherein the SSRI is administered orally in an amount between about 10 mg–2500 mg/daily.

13. The method of reducing a platelet activation state of an individual comprising administering to the individual an effective amount of at least one SSRI, wherein the SSRI prevents the reduction of serotonin in blood of the individual, and the SSRI is selected from the group consisting of sertraline, a sertraline metabolite, fluvoxamine, a fluvoxamine metabolite, paroxetine, a paroxetine metabolite, fluoxetine, and a fluoxetine metabolite, thereby reducing at least one platelet activation marker.

14. The method of claim 13, wherein the individual is at risk for a vascular event, disease or disorder.

15. The method of claim 14, wherein the vascular event is selected from the group consisting of: myocardial infarction, angina, stroke, pulmonary embolism, transient ischemic attack, deep vein thrombosis, thrombotic re-occlusion subsequent to a coronary intervention procedure, heart surgery or vascular surgery, peripheral vascular thrombosis, Syndrome X, heart failure, and a disorder in which a narrowing of at least one coronary artery occurs.

16. A method of inhibiting or reducing platelet activation comprising contacting at least one SSRI with platelets in an amount sufficient to inhibit or reduce the platelet activation, wherein the SSRI is selected from the group consisting of sertraline, a sertraline metabolite, fluvoxamine, a fluvoxamine metabolite, paroxetine, a paroxetine metabolite, fluoxetine, and a fluoxetine metabolite.

17. The method of claim 16, wherein at least one platelet activation marker is reduced.

18. The method of claim 17, wherein the platelet activation marker is reduced by at least about 10%.

19. A method of preventing or treating an individual at risk for a vascular event, disease or disorder, comprising administering to the individual an effective amount of at least one SSRI and at least one other composition used for treating or preventing a vascular event, wherein the SSRI prevents the reduction of serotonin in blood of the individual, and the SSRI is selected from the group consisting of sertraline, a sertraline metabolite, fluvoxamine, a fluvoxamine metabolite, paroxetine, a paroxetine metabolite, fluoxetine, and a fluoxetine metabolite.

20. The method of claim 19, wherein the other composition used for treating or preventing a vascular event is selected from the group consisting of aspirin, heparin, thienopyridine and a GPIIb/IIIa inhibitor.

21. The method of claim 19, wherein the vascular event is selected from a group consisting of: myocardial infarction, angina, stroke, pulmonary embolism, transient ischemic attack, deep vein thrombosis, thrombotic re-occlusion subsequent to a coronary intervention procedure, heart surgery or vascular surgery, peripheral vascular thrombosis, Syndrome X, heart failure, and a disorder in which a narrowing of at least one coronary artery occurs.

22. The method of claim 21, wherein sertraline is administered orally, by injection, intravenously, intramuscularly, subcutaneously, parenterally, nasally, by inhalation, by implant, or by suppository.

23. The method of claim 22, wherein the SSRI is administered orally in an amount between about 10 mg–2500 mg/daily.

24. The method of claim 23, comprising comparing the level of at least one platelet activation marker from a sample taken from the individual to a control.

* * * * *